(12) United States Patent
Salman et al.

(10) Patent No.: US 7,544,708 B2
(45) Date of Patent: Jun. 9, 2009

(54) AZABICYCLO DERIVATIVES AS MUSCARINIC RECEPTOR ANTAGONISTS

(75) Inventors: Mohammad Salman, Haryana (IN);
Anita Mehta, Buffalo Grove, IL (US);
Pakala Kumara Savithru Sarma, Haryana (IN); Shankar Jayram Shetty, Haryana (IN); Sankaranarayanan Dharmarajan, Haryana (IN); Naresh Kumar, Haryana (IN); Arundutt Vishwanatham Silamkoti, Secunderabad (IN); Anita Chugh, Delhi (IN)

(73) Assignee: Ranbaxy Laboratories Limited, Gugaon (IN)

( * ) Notice: Subject to any disclaimer, the term of this patent is extended or adjusted under 35 U.S.C. 154(b) by 490 days.

(21) Appl. No.: 10/520,572

(22) PCT Filed: Apr. 11, 2003

(86) PCT No.: PCT/IB03/01367

§ 371 (c)(1),
(2), (4) Date: Jan. 19, 2006

(87) PCT Pub. No.: WO2004/005252

PCT Pub. Date: Jan. 15, 2004

(65) Prior Publication Data

US 2006/0111425 A1    May 25, 2006

(30) Foreign Application Priority Data

Jul. 8, 2002    (WO) ........................ PCT/IB02/02663

(51) Int. Cl.
*A61K 31/40*    (2006.01)
*C07D 209/44*    (2006.01)
(52) U.S. Cl. ........................ 514/412; 548/515
(58) Field of Classification Search ................. 514/412; 548/515
See application file for complete search history.

(56) References Cited

U.S. PATENT DOCUMENTS

| | | | |
|---|---|---|---|
| 2,490,714 A | 12/1949 | Searle | 260/239 |
| 3,176,019 A | 3/1965 | Campbell et al. | 260/293.4 |
| 5,001,160 A | 3/1991 | McPherson et al. | 514/255 |
| 5,164,402 A | 11/1992 | Brighty | 514/300 |
| 5,179,108 A | 1/1993 | George et al. | 514/319 |
| 5,281,601 A | 1/1994 | Cross et al. | 514/320 |
| 5,397,800 A | 3/1995 | Alker et al. | 514/413 |
| 5,559,269 A | 9/1996 | Johansson et al. | 564/443 |
| 5,948,792 A | 9/1999 | Tsuchiya et al. | 514/317 |
| 6,130,232 A | 10/2000 | Mase et al. | 514/318 |
| 6,174,900 B1 | 1/2001 | Okada et al. | 514/317 |
| 6,313,312 B1 | 11/2001 | Banks et al. | 548/452 |
| 7,232,835 B2 | 6/2007 | Mehta et al. | 514/323 |
| 7,288,562 B2 * | 10/2007 | Mehta et al. | 514/412 |
| 2003/0105071 A1 | 6/2003 | Cuny et al. | 514/210.2 |
| 2003/0162780 A1 | 8/2003 | Brotherton-Pleiss et al. | 514/235.5 |
| 2003/0171362 A1 | 9/2003 | Madera et al. | 514/218 |
| 2006/0247225 A1 | 11/2006 | Mehta et al. | 514/213.01 |
| 2006/0281805 A1 | 12/2006 | Mehta et al. | 514/412 |
| 2006/0287380 A1 | 12/2006 | Salman et al. | 514/412 |
| 2007/0010568 A1 | 1/2007 | Mehta et al. | 514/412 |
| 2007/0135508 A1 | 6/2007 | Mehta et al. | 514/412 |

FOREIGN PATENT DOCUMENTS

| | | |
|---|---|---|
| CA | 2155320 | 8/1993 |
| EP | 0 325 571 | 7/1989 |
| EP | 0 388 054 | 9/1990 |
| EP | 0 413 455 | 2/1991 |
| EP | 0 613 232 | 8/1994 |
| EP | 0 801 067 | 10/1997 |
| EP | 0 823 423 | 2/1998 |
| EP | 0 863 141 | 9/1998 |
| GB | 940540 | 10/1963 |
| JP | 92921/1994 | 4/1994 |
| JP | 135958/1994 | 5/1994 |
| WO | WO 91/09013 | 6/1991 |
| WO | WO 93/16018 | 8/1993 |
| WO | WO 93/16048 | 8/1993 |
| WO | WO 96/33973 | 10/1996 |
| WO | WO 97/45414 | 12/1997 |
| WO | WO 98/00016 | 1/1998 |
| WO | WO 98/00109 | 1/1998 |
| WO | WO 98/00132 | 1/1998 |
| WO | WO 98/05641 | 2/1998 |
| WO | WO 98/29402 | 7/1998 |
| WO | WO 98/00133 | 1/1999 |

(Continued)

OTHER PUBLICATIONS

Morissette et al., Advanced Drug Delivery Reviews, 2004, 56, 275-300, especially p. 275.*

(Continued)

*Primary Examiner*—Golam M M Shameem
*Assistant Examiner*—Susannah Chung
(74) *Attorney, Agent, or Firm*—George E. Heibel, Esq.

(57) ABSTRACT

This invention generally relates to muscarinic receptor antagonists which are useful, among other uses, for the treatment of various diseases of the respiratory, urinary and gastrointestinal systems mediated through muscarinic receptors. Specifically, the invention relates to derivatives of azabicyclo compounds, including, for example, 6-substituted azabicyclo [3.1.0] hexanes, and 2,4,6-trisubstituted derivatives. The invention also relates to pharmaceutical compositions containing the compounds and the methods of treating the diseases mediated through muscarinic receptors.

7 Claims, No Drawings

FOREIGN PATENT DOCUMENTS

| | | |
|---|---|---|
| WO | WO 99/43657 | 9/1999 |
| WO | WO 98/53814 | 12/1999 |
| WO | WO 01/42212 | 6/2001 |
| WO | WO 01/42213 | 6/2001 |
| WO | WO 01/47893 | 7/2001 |
| WO | WO 01/90081 | 11/2001 |
| WO | WO 01/090082 | 11/2001 |
| WO | WO 02/00652 | 1/2002 |
| WO | WO 02/04402 | 1/2002 |
| WO | WO 02/06241 | 1/2002 |
| WO | WO 02/51841 | 7/2002 |
| WO | WO 02/53564 | 7/2002 |
| WO | WO 03/033495 | 4/2003 |
| WO | WO 03/048124 | 6/2003 |
| WO | WO 03/048125 | 6/2003 |
| WO | WO 2004/004629 | 1/2004 |
| WO | WO 2004/005252 | 1/2004 |
| WO | WO 2004/014363 | 2/2004 |
| WO | WO 2004/014853 | 2/2004 |
| WO | WO 2004/018422 | 3/2004 |
| WO | WO 2004/052857 | 6/2004 |
| WO | WO 2004/056767 | 7/2004 |
| WO | WO 2004/056810 | 7/2004 |
| WO | WO 2004/056811 | 7/2004 |
| WO | WO 2004/067510 | 8/2004 |
| WO | WO 2004/069835 | 8/2004 |
| WO | WO 2004/089363 | 10/2004 |
| WO | WO 2004/089898 | 10/2004 |
| WO | WO 2004/089899 | 10/2004 |
| WO | WO 2004/089900 | 10/2004 |
| WO | WO 2005/092341 | 10/2005 |
| WO | WO 2005/003587 | 1/2006 |
| WO | WO 2006/035282 | 4/2006 |
| WO | WO 2006/064304 | 6/2006 |

OTHER PUBLICATIONS

Patani et al., Chem Rev, 1996, vol. 96 (8), pp. 3147-3176, especially p. 3170.* de Groat and Yoshimura, "Pharmacology of the Lower Urinary Tract", *Annual Review of Pharmacology and Toxicology*, 41:691-721 (2001).

Cheng and Prusoff, "Relationship between the inhibition constant ($K_1$) and the concentration of inhibitor which causes 50 per cent inhibition ($I_{50}$) of an enzymatic reaction", *Biochemical Pharmacology*, 22:3099-3108 (1973).

Birdsall et al., "Muscarinic receptors: it's a knockout", *Trends in Pharmacological Sciences*, 22(5):215-219 (2001).

Brighty et al., "Synthesis of (1α,5α,6α)-6-Amino-3-azabicyclo[3.1.0]hexane, a Novel Achiral Diamine", *Synlett*, 1097-1099 (1996).

Braish et al., "Construction of the (1α,5α,6α)-6-Amino-3-azabicyclo[3.1.0]hexane Ring System", *Synlett*, 1100-1102 (1996).

Chapple, "Muscarinic receptor antagonists in the treatment of overactive bladder", *Urology*, 55(Suppl. 5A):33-46 (2000).

Eglen et al., "Muscarinic receptor ligands and their theraputic potential", *Current Opinion in Chemical Biology*, 3:426-432 (1999).

Eglen et al., "Theraputic opportunities from muscarinic receptor research", *Trends in Pharmacological Sciences*, 22(8):409-414 (2001).

Felder et al., "Theraputic Opportunities for Muscarinic Receptors in the Central Nervous System", *Journal of Medicinal Chemistry*, 43(23):4333-4353 (2000).

Grover et al., "Chiral Mandelic Acid Template Provides a Highly Practical Solution for (S)-Oxybutynin Synthesis", *Journal of Organic Chemistry*, 65:6283-6287 (2000).

Shacklett and Smith, "The Preparation of Substituted Benzilic Acids", *Journal of the American Chemical Society*, 75:2654-2657 (1953).

Sagara et al., "Cyclohexylmethylpiperidinyltriphenylpropioamide: A Selective Muscarinic $M_3$ Antagonist Discriminating against the Other Receptor Subtypes", *Journal of Medicinal Chemistry*, 45:984-987 (2002).

Nkpa and Chedekel, "Mechanistic Studies on the Addition of Cysteine to 3,4-Dihydroxyphenylalanine", *Journal of Organic Chemistry*, 46:213-215 (1981).

Kadin and Cannon, "Esters of N-Methyl-3-hydroxypiperidine Having Psychotomimetic Activity. II", *Journal of Organic Chemistry*, 27:240-245 (1962).

Broadley and Kelly, "Muscarinic Receptor Agonists and Antagonists", *Molecules*, 6:142-193 (2001).

Moriya et al., "Affinity Profiles of Various Muscarinic Antagonists for Cloned Human Muscarinic Acetylcholine Receptor (mAChR) Subtypes and mAChRs in Rat Heart and Submandibular Gland", *Life Sciences*, 64(25):2351-2358 (1999).

Kubo et al., "Cloning, sequencing and expression of complementary DNA encoding the muscarinic acetylcholine receptor", *Nature*, 323(2):411-416 (1986).

Bonner et al., "Identification of a Family of Muscarinic Acetylcholine Receptor Genes", *Science*, 237:527-531 (1987).

Steers, "The future direction of neuro-urology drug research", *Current Opinion in CPNS Investigational Drugs*, 2(3):268-282.

Steers, Barrot, Wein, "Voiding dysfunction: diagnosis classification and management", In: *Adult and Pediatric Urology*, ed. Gillenwater, Grayhack, Howards, Duckett. Mosby, St. Louis, MO; 1220-1325, 3rd edition (1996).

Weinstock et al., "A General, One-Step Synthesis of α-keto Esters", *Synthetic Communications*, 11(12):943-946 (1981).

Vogel's textbook, "Practical Organic Chemistry" 1046-1047 (5th Ed.).

"Design of prodrugs", ed. H. Bundgaard, Elsevier (1985).

Wess et al., "Muscarinic receptor subtypes mediating central and peripheral antinociception studied with muscarinic receptor knockout mice: A review", *Life Sciences*, 72:2047-2054 (2003).

O'Neill, "Unusual suspect for antipsychotic-induced diabetes", *Drug Discovery Today*, 10(20):1338 (2005).

Michel and Hegde, "Treatment of the overactive bladder syndrome with muscarinic receptor antagonists—a matter of metabolites?", *Naunyn-Schmiedeberg's Arch Pharmacol*, 374:79-85 (2006).

Latifpour et al., "Effects of Experimental Diabetes on Biochemical and Functional Characteristics of Bladder Muscarinic Receptors", *The Journal of Pharmacology and Experimental Therapeutics*, 248(1):81-88 (1989).

Carrier and Aronstam, "Altered Muscarinic Receptor Properties and Function in the Heart in Diabetes", *The Journal of Pharmacology and Experimental Therapeutics*, 242(2):531-535 (1987).

Ahrén et al., "Blockade of muscarinic transmission increases the frequency of diabetes after low-dose alloxan challenge in the mouse", *Diabetologia*, 39:383-390 (1996).

Abrams et al., "Muscarinic receptors: their distribution and function in body systems, and the implications for treating overactive bladder", *British Journal of Pharmacology*, 148(5):565-578 (2006).

Kaiser et al, "Synthesis and Antimuscarinic Activity of Some 1-Cycloalkyl-1-hydroxy-1-phenyl-3-(4-substituted piperazinyl)-2-propanones and Related Compounds", *Journal of Medicinal Chemistry*, 36(5):610-616 (1993).

Carter et al, "Analogues of Oxybutynin. Synthesis and Antimuscarinic and Bladder Activity of Some Substituted 7-Amino-1-hydroxy-5-heptyn-2-ones and Related Compounds", *Journal of Medicinal Chemistry*, 34(10):3065-3074 (1991).

Morissette et al, "High-throughput crystallization: polymorphs, salts, co-crystals and solvates of pharmaceutical solids", *Advanced Drug Delivery Reviews*, 56:275-300 (2004).

Andersson et al., "Asymmetric Total Synthesis of (+)-Tolterodine, a New Muscarinic Receptor Antagonist, via Copper-Assisted Asymmetric Conjugate Addition of Aryl Grignard Reagents to 3-Phenyl-prop-2-enoyl-oxazolidinones", *Journal of Organic Chemistry*, 63(22):8067-8070 (1998).

* cited by examiner

AZABICYCLO DERIVATIVES AS MUSCARINIC RECEPTOR ANTAGONISTS

FIELD OF THE INVENTION

This invention generally relates to muscarinic receptor antagonists which are useful, among other uses, for the treatment of various diseases of the respiratory, urinary and gastrointestinal systems mediated through muscarinic receptors. Specifically, the invention relates to derivatives of azabicyclo compounds, including, for example, 6-substituted azabicyclo [3.1.0] hexanes, 2,6- and 4,6-disubstituted derivatives, and 2,4,6-trisubstituted derivatives, as well as pharmaceutical compositions containing such compounds and methods of treating diseases mediated through muscarinic receptors.

BACKGROUND OF THE INVENTION

Muscarinic receptors as members of the G Protein Coupled Receptors (GPCRs) are composed of a family of 5 receptor sub-types ($M_1$, $M_2$, $M_3$, $M_4$ and $M_5$) and are activated by the neurotransmitter acetylcholine. These receptors are widely distributed on multiple organs and tissues and are critical to the maintenance of central and peripheral cholinergic neurotransmission. The regional distribution of these receptor sub-types in the brain and other organs has been documented. For example, the $M_1$ subtype is located primarily in neuronal tissues such as cereberal cortex and autonomic ganglia, the $M_2$ subtype is present mainly in the heart where it mediates cholinergically induced bradycardia, and the $M_3$ subtype is located predominantly on smooth muscle and salivary glands (*Nature*, 323, p. 411 (1986); *Science*, 237, p. 527 (1987)).

A review in *Current Opinions in Chemical Biology*, 3, p. 426 (1999), as well as in *Trends in Pharmacological Sciences*, 22, p. 409 (2001) by Eglen et. al., describes the biological potentials of modulating muscarinic receptor sub-types by ligands in different disease conditions, such as Alzheimer's Disease, pain, urinary disease condition, chronic obstructive pulmonary disease, and the like.

A review in *J. Med. Chem.*, 43, p. 4333 (2000), by Felder et. al. describes therapeutic opportunities for muscarinic receptors in the central nervous system and elaborates on muscarinic receptor structure and function, pharmacology and their therapeutic uses.

The pharmacological and medical aspects of the muscarinic class of acetylcholine agonists and antagonists are presented in a review in *Molecules*, 6, p. 142 (2001).

Birdsall et. al. in *Trends in Pharmacological Sciences*, 22, p. 215 (2001) have also summarized the recent developments on the role of different muscarinic receptor subtypes using different muscarinic receptor of knock out mice.

Muscarinic agonists such as muscarine and pilocarpine and antagonists such as atropine have been known for over a century, but little progress has been made in the discovery of receptor subtype-selective compounds, making it difficult to assign specific functions to the individual receptors. Although classical muscarinic antagonists such as atropine are potent bronchodilators, their clinical utility is limited due to high incidence of both peripheral and central adverse effects such as tachycardia, blurred vision, dryness of mouth, constipation, dementia, etc. Subsequent development of the quarterly derivatives of atropine such as ipratropium bromide are better tolerated than parenterally administered options, but most of these are not ideal anti-cholinergic bronchodilators, due to lack of selectivity for muscarinic receptor sub-types, resulting in dose-limiting side-effects such as thirst, nausea, mydriasis and those associated with the heart such as tachycardia mediated by the $M_2$ receptor.

*Annual Review of pharmacological Toxicol.*, 41, p. 691 (2001), describes the pharmacology of the lower urinary tract infections. Although anti-muscarinic agents such as oxybutynin and tolterodine that act non-selectively on muscarinic receptors have been used for many years to treat bladder hyperactivity, the clinical effectiveness of these agents has been limited due to the side effects such as dry mouth, blurred vision and constipation. Tolterodine is considered to be generally better tolerated than oxybutynin. (Steers et. al., in *Curr. Opin. Invest. Drugs*, 2, 268; Chapple et. al., in *Urology*, 55, 33; Steers et al., *Adult and Pediatric Urology*, ed. Gillenwatter et al., pp 1220-1325, St. Louis, Mo.; Mosby. $3^{rd}$ edition (1996)).

There remains a need for development of new highly selective muscarinic antagonists which can interact with distinct subtypes, thus avoiding the occurrence of adverse effects.

Compounds having antagonistic activity against muscarinic receptors have been described in Japanese patent application Laid Open Number 92921/1994 and 135958/1994; WO 93/16048; U.S. Pat. No. 3,176,019; GB 940,540; EP 0325 571; WO 98/29402; EP 0801067; EP 0388054; WO 9109013; U.S. Pat. No. 5,281,601. Also, U.S. Pat. Nos. 6,174, 900, 6,130,232 and 5,948,792; WO 97/45414 are related to 1,4-disubstituted piperidine derivatives; WO 98/05641 describes fluorinated, 1,4-disubstitued piperidine derivatives; WO 93/16018 and WO96/33973 are other references of interest.

A report in *J. Med. Chem.*, 4, p. 984 (2002), describes cyclohexylmethyl piperidinyl triphenylpropioamide derivatives as selective $M_3$ antagonist discriminating against the other receptor subtypes.

SUMMARY OF THE INVENTION

In one aspect, azabicyclo derivatives, including, for example, 6-substituted azabicyclo[3.1.0]hexanes, 2,6- and 4,6-disubstituted derivatives, and 2,4,6-trisubstituted derivatives, are provided as muscarinic receptor antagonists which can be useful as safe and effective therapeutic or prophylactic agents for the treatment of various diseases of the respiratory, urinary and gastrointestinal systems. Also provided are processes for synthesizing such compounds.

In another aspect, pharmaceutical compositions containing such compounds are provided together with acceptable carriers, excipients or diluents which can be useful for the treatment of various diseases of the respiratory, urinary and gastrointestinal systems.

The enantiomers, diastereomers, N-oxides, polymorphs, pharmaceutically acceptable salts and pharmaceutically acceptable solvates of these compounds as well as metabolites having the same type of activity are also provided, as well as pharmaceutical compositions comprising the compounds, their metabolites, enantiomers, diastereomers, N-oxides, polymorphs, solvates or pharmaceutically acceptable salts thereof, in combination with a pharmaceutically acceptable carrier and optionally included excipients.

Other aspects will be set forth in the description which follows, and in part will be apparent from the description or may be learnt by the practice of the invention.

In accordance with one aspect, there are provided compounds having the structure of Formula I:

Formula I

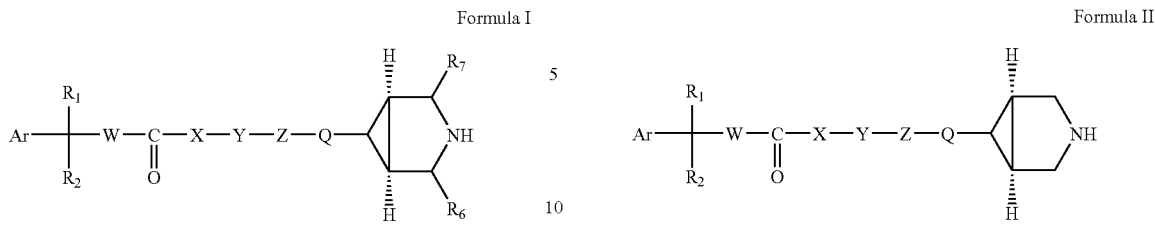

and their pharmaceutically acceptable salts, pharmaceutically acceptable solvates, esters, enantiomers, diastereomers, N-oxides, polymorphs, metabolites, wherein Ar represents an aryl or a heteroaryl ring having 1-2 hetero atoms selected from the group consisting of oxygen, sulphur and nitrogen atoms, the aryl or heteroaryl rings may be unsubstituted or substituted by one to three substituents independently selected from lower alkyl ($C_1$-$C_4$), lower perhalo alkyl ($C_1$-$C_4$), cyano, hydroxy, nitro, lower alkoxy ($C_1$-$C_4$), lower perhalo alkoxy ($C_1$-$C_4$), unsubstituted amino, N-lower alkyl ($C_1$-$C_4$) or -aryl amino, amino carbonyl, or N-lower alkyl ($C_1$-$C_4$) or -aryl amino carbonyl;

$R_1$ represents a hydrogen, hydroxy, hydroxy methyl, substituted or unsubstituted amino, alkoxy, carbamoyl or halogen (e.g. fluorine, chlorine, bromine and iodine);

$R_2$ represents alkyl, $C_3$-$C_7$ cycloalkyl ring, a $C_3$-$C_7$ cyclo alkenyl ring, an aryl, heterocyclic or a heteroaryl ring having 1 to 2 hetero atoms selected from a group consisting of oxygen, sulphur and nitrogen atoms; the aryl, heteroaryl, heterocyclic or a cycloalkyl ring may be unsubstituted or substituted by one to three substituents independently selected from lower alkyl ($C_1$-$C_4$), lower perhalo alkyl ($C_1$-$C_4$), cyano, hydroxy, nitro, lower alkoxycarbonyl, halogen, lower alkoxy ($C_1$-$C_4$), lower perhalo alkoxy ($C_1$-$C_4$), unsubstituted amino, N-lower alkyl ($C_1$-$C_4$) or -aryl amino, amino carbonyl, or N-lower alkyl ($C_1$-$C_4$) or -aryl amino carbonyl;

W represents $(CH_2)_p$, wherein p represents 0 to 1;

X represents an oxygen, sulphur, —NR or no atom, wherein R represents hydrogen or ($C_{1-6}$) alkyl;

Y represents $CHR_5CO$ or $(CH_2)_q$ wherein $R_5$ represents hydrogen or methyl and q represents 0 to 4;

Z represents oxygen, sulphur, or $NR_{10}$, wherein $R_{10}$ represents hydrogen, or $C_{1-6}$ alkyl;

Q represents $(CH_2)_n$ (wherein n represents 0 to 4), $CHR_8$ (wherein $R_8$ represents H, OH, $C_{1-6}$ alkyl, $C_{1-6}$ alkenyl, $C_{1-6}$ alkoxy) or $CH_2CHR_9$ (wherein $R_9$ represents H, OH, lower alkyl ($C_1$-$C_4$) or lower alkoxy ($C_1$-$C_4$)); and $R_6$ and $R_7$ are independently selected from H, $CH_3$, COOH, $CONH_2$, $NH_2$, and $CH_2NH_2$ In accordance with a second aspect, there are provided compounds having the structure of Formula II (Formula I, when $R_6$ and $R_7$=H) and their pharmaceutically acceptable salts, pharmaceutically acceptable solvates, esters, enantiomers, diastereomers, N-oxides, polymorphs, or metabolites, wherein Ar, $R_1$, $R_2$, W, X, Y, Z and Q are as defined for Formula I.

Formula II

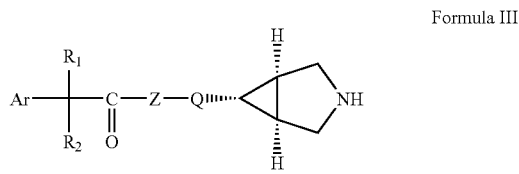

In accordance with a third aspect, there are provided compounds having the structure of Formula III (Formula I wherein W is $(CH_2)p$ where p=0, X is no atom and Y is $(CH_2)q$ where q=0, $R_6$=H, $R_7$=H) and their pharmaceutically acceptable salts, pharmaceutically acceptable solvates, esters, enantiomers, diastereomers, N-oxides, polymorphs, or metabolites, wherein Ar, $R_1$, $R_2$, Z and Q are as defined for Formula I.

Formula III

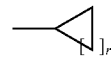

In accordance with a fourth aspect, there are provided compounds having the structure of Formula IV (Formula I wherein W is $(CH_2)p$ where p=0, X is no atom and Y is $(CH_2)q$ where q=0, $R_6$=H, $R_7$=H, $R_2$=

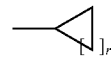

) and their pharmaceutically acceptable salts, pharmaceutically acceptable solvates, esters, enantiomers, diastereomers, N-oxides, polymorphs, or metabolites, wherein Ar, $R_1$, Z and Q are as defined for Formula I and r is 1 to 4.

Formula IV

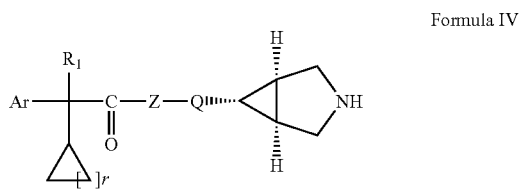

In accordance with a fifth aspect, there are provided compounds having the structure of Formula V (Formula I wherein W is $(CH_2)p$ where p=0, X is no atom and Y is $(CH_2)q$ where q=0, $R_6$=H, $R_7$=H, $R_2$=

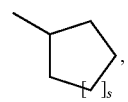

, $R_1$ is hydroxy, Ar is phenyl), and their pharmaceutically acceptable salts, pharmaceutically acceptable solvates, esters, enantiomers, diastereomers, N-oxides, polymorphs, or metabolites, wherein Z and Q are the same as defined for Formula I, s represents 1 or 2.

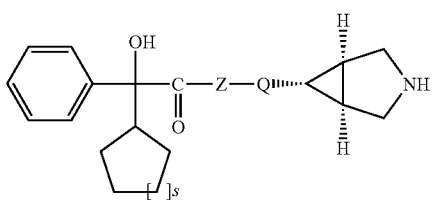

Formula V

In accordance with a sixth aspect, there is provided a method for treatment or prophylaxis of an animal or a human suffering from a disease or disorder of the respiratory, urinary and gastrointestinal systems, wherein the disease or disorder is mediated through muscarinic receptors. The method includes administration of at least one compound having the structure of Formula I.

In accordance with a seventh aspect, there is provided a method for treatment or prophylaxis of an animal or a human suffering from a disease or disorder associated with muscarinic receptors, comprising administering to a patient in need thereof, an effective amount of a muscarinic receptor antagonist compound as described above.

In accordance with an eighth aspect, there is provided a method for treatment or prophylaxis of an animal or a human suffering from a disease or disorder of the respiratory system such as bronchial asthma, chronic obstructive pulmonary disorders (COPD), pulmonary fibrosis, and the like; urinary system which induce such urinary disorders as urinary incontinence, lower urinary tract symptoms (LUTS), etc.; and gastrointestinal system such as irritable bowel syndrome, obesity, diabetes and gastrointestinal hyperkinesis with compounds as described above, wherein the disease or disorder is associated with muscarinic receptors.

In accordance with a ninth aspect, there are provided processes for preparing the compounds as described above.

The compounds described herein exhibit significant potency in terms of their activity, as determined by in vitro receptor binding and functional assays and in vivo experiments using anaesthetized rabbits. The compounds that were found active in vitro were tested in vivo. Some of the compounds are potent muscarinic receptor antagonists with high affinity towards $M_3$ receptors. Therefore, pharmaceutical compositions for the possible treatment for the disease or disorders associated with muscarinic receptors are provided. In addition, the compounds can be administered orally or parenterally.

DETAILED DESCRIPTION OF THE INVENTION

The compounds presented herein may be prepared by methods represented by the following reaction sequences:

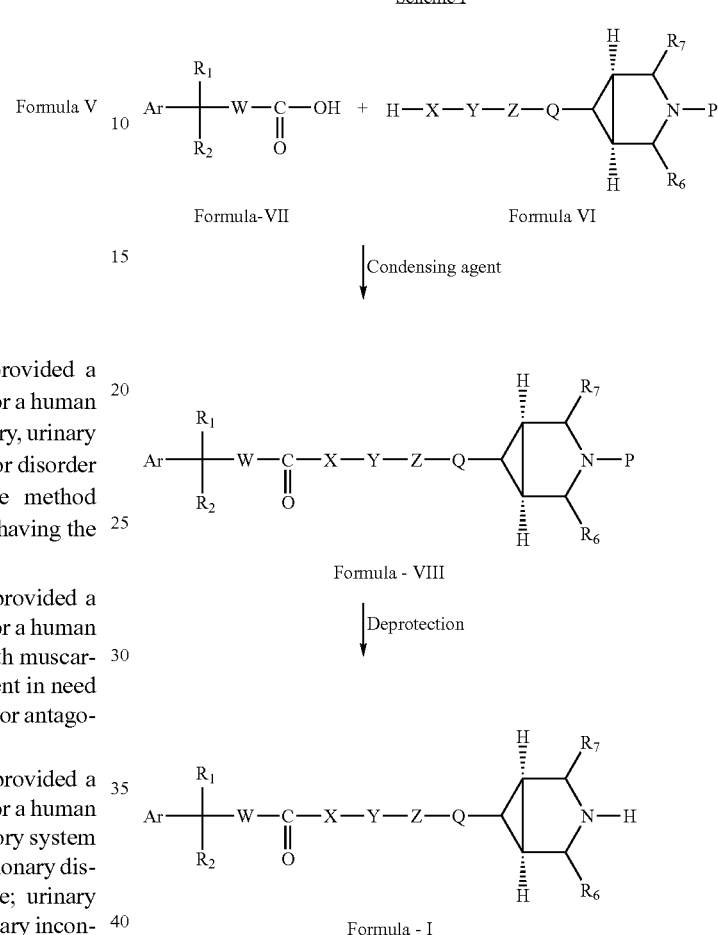

The compounds of Formula I may be prepared, for example, by the reaction sequence as shown in Scheme I. The preparation comprises reacting a compound of Formula VII with a compound of Formula VI, wherein Ar represents an aryl or a heteroaryl ring having 1-2 hetero atoms (such as oxygen, sulphur or nitrogen atoms), where the aryl or heteroaryl rings may be unsubstituted or substituted by one to three substituents independently selected from lower alkyl ($C_1$-$C_4$), lower perhalo alkyl ($C_1$-$C_4$), cyano, hydroxy, nitro, lower alkoxy ($C_1$-$C_4$), lower perhalo alkoxy ($C_1$-$C_4$), unsubstituted amino, N-lower alkyl ($C_1$-$C_4$) or -aryl amino, amino carbonyl, or N-lower alkyl ($C_1$-$C_4$) or -aryl amino carbonyl;

$R_1$ represents a hydrogen, hydroxy, hydroxy methyl, substituted or unsubstituted amino, alkoxy, carbamoyl or halogen (e.g. fluorine, chlorine, bromine and iodine);

$R_2$ represents alkyl, $C_3$-$C_7$ cycloalkyl ring, a $C_3$-$C_7$ cyclo alkenyl ring, an aryl, heterocyclic or a heteroaryl ring having 1 to 2 hetero atoms; the aryl, heteroaryl, heterocyclic or a cycloalkyl ring may be unsubstituted or substituted by one to three substituents independently selected from lower alkyl ($C_1$-$C_4$), lower perhalo alkyl ($C_1$-$C_4$), cyano, hydroxy, nitro, lower alkoxycarbonyl, halogen, lower alkoxy ($C_1$-$C_4$), lower perhalo alkoxy ($C_1$-$C_4$), unsubstituted amino, N-lower alkyl ($C_1$-$C_4$) or -aryl amino, amino carbonyl, or N-lower alkyl ($C_1$-$C_4$) or -aryl amino carbonyl;

W represents $(CH_2)_p$, wherein p represents 0 to 1;

X represents an oxygen, sulphur, —NR or no atom, wherein R represents hydrogen or ($C_{1-6}$) alkyl;

Y represents $CHR_5CO$ or $(CH_2)q$ wherein $R_5$ represents hydrogen or methyl and q represents 0 to 4;

Z represents oxygen, sulphur, or $NR_{10}$, wherein $R_{10}$ represents hydrogen, $C_{1-6}$ or alkyl;

Q represents —$(CH_2)_n$— (wherein n represents 0 to 4), $CHR_8$ (wherein $R_8$ represents H, OH, $C_{1-6}$, alkyl, $C_{1-6}$ alkenyl, $C_{1-6}$ alkoxy) or $CH_2CHR_9$ (wherein $R_9$ represents H, OH, lower alkyl ($C_1$-$C_4$) or lower alkoxy ($C_1$-$C_4$));

$R_6$ and $R_7$ are independently selected from H, $CH_3$, COOH, $CONH_2$, $NH_2$, and $CH_2NH_2$; and P is any protecting group for an amino group, for example, benzyl or t-butyloxy carbonyl groups.

The reaction between a compound of Formula VII and a compound of Formula VI can take place in the presence of a condensing agent (for example, 1-(3-dimethylaminopropyl)-3-ethyl carbodiimide hydrochloride (EDC) or 1,8-diazabicyclo [5.4.0]undec-7-ene (DBU)), in a solvent (such as N,N-dimethylformamide, dimethylsulfoxide, toluene, or xylene, at temperatures ranging from about 0 to about 140° C.), to give a protected compound of Formula VIII which on deprotection in the presence of a deprotecting agent (for example, palladium on carbon, trifluoroacetic acid (TFA) or hydrochloric acid) in an organic solvent (for example, methanol, ethanol, tetrahydrofuran or acetonitrile, at temperatures ranging from about 10 to about 50° C.) gives an unprotected compound of Formula I.

In the above scheme, where specific bases, condensing agents, protecting groups, deprotecting agents, solvents, catalysts, temperatures, etc. are mentioned, it is to be understood that other bases, condensing agents, protecting groups, deprotecting agents, solvents, catalysts, temperatures, etc. known to those skilled in the art may be used. Similarly, the reaction temperature and duration may be adjusted according to the desired needs.

Suitable salts of the compounds represented by the Formula I were prepared so as to solubilize the compound in aqueous medium for biological evaluations, as well as to be compatible with various dosage formulations and also to aid in the bioavailability of the compounds. Examples of such salts include pharmacologically acceptable salts such as inorganic acid salts (for example, hydrochloride, hydrobromide, sulphate, nitrate and phosphate), organic acid salts (for example, acetate, tartarate, citrate, fumarate, maleate, tolounesulphonate and methanesulphonate). When carboxyl groups are included in the Formula I as substituents, they may be present in the form of an alkaline or alkali metal salt (for example, sodium, potassium, calcium, magnesium, and the like). These salts may be prepared by various techniques, such as treating the compound with an equivalent amount of inorganic or organic, acid or base in a suitable solvent.

Particular compounds are shown here:

(2R,2S) (1α,5α,6α)-N-[3-azabicyclo[3.1.0]hexyl-6-(aminomethyl)-yl]-2-hydroxy-2-cyclopentyl-2-phenyl acetamide (Compound 1);

(2R,2S) (1α,5α,6α)-N-[3-azabicyclo[3.1.0]hexyl-6-(aminomethyl)-yl]-2-hydroxy-2-cyclopentyl-2-phenyl acetamide hydrochloride salt (Compound 2);

(2R)-(1α,5α,6α)-N-[3-azabicyclo[3.1.0]hexyl-6-(aminomethyl)-yl]-2-hydroxy-2-cyclopentyl 2-phenyl acetamide (Compound 3);

(2R)-(1α,5α,6α)-N-[3-azabicyclo[3.1.0]hexyl-6-(aminomethyl)-yl]-2-hydroxy-2-cyclopentyl 2-phenyl acetamide hydrochloride salt (Compound 4);

(2S)-(1α,5α,6α)-N-[3-azabicyclo[3.1.0]hexyl-6-(aminomethyl)-yl]-2-hydroxy-2-cyclopentyl 2-phenyl acetamide (Compound 5);

(2S)-(1α,5α,6α)-N-[3-azabicyclo[3.1.0]hexyl-6-(aminomethyl)-yl]-2-hydroxy-2-cyclopentyl 2-phenyl acetamide hydrochloride salt (Compound 6);

(2R,2S) (1α,5α,6α)-N-[3-azabicyclo[3.1.0]hexyl-6-(aminomethyl)-yl]-2-methoxy-2-cyclopentyl-2-phenyl acetamide (Compound 7);

(2R,2S) (1α,5α,6α)-N-[3-azabicyclo[3.1.0]hexyl-6-(aminomethyl)-yl]-2-hydroxy-2-cycloheptyl-2-phenyl acetamide (Compound 8);

(2R,2S) (1α,5α,6α)-N-[3-azabicyclo[3.1.0]hexyl-6-(aminomethyl)-yl]-2-hydroxy-2-cyclobutyl-2-phenyl acetamide (Compound 9);

(2R,2S) (1α,5α,6α)-N-[3-azabicyclo[3.1.0]hexyl-6-(aminomethyl)-yl]-2-hydroxy-2-cyclobutyl-2-phenyl acetamide tartarate salt (Compound 10);

(2R) (1α,5α,6α)-N-[3-azabicyclo[3.1.0]hexyl-6-(aminomethyl)-yl]-2-hydroxy-2-(3,3-difluorocyclopentyl)-2-phenyl acetamide (Compound 11);

(2R,2S) (1α,5α,6α)-N-[3-azabicyclo[3.1.0]hexyl-6-(aminomethyl)-yl]-2-hydroxy-2-(3-fluorocyclopentyl)-2-phenyl acetamide (Compound 12);

(2R,2S) (1α,5α,6α)-N-[3-azabicyclo[3.1.0]hexyl-6-(aminomethyl)-yl]-2-hydroxy-2-(3,3-difluorocyclopentyl)-2-phenyl acetamide (Compound 13);

(2R,2S) (1α,5α,6α)-N-[3-azabicyclo[3.1.0]hexyl-6-(aminomethyl)-yl]-2-hydroxy-2-(3,3-difluorocyclopentyl)-2-phenyl acetamide tartarate salt (Compound 14);

(2R,2S) (1α,5α,6α)-N-[3-azabicyclo[3.1.0]hexyl-6-(aminomethyl)-yl]-2-hydroxy-2,2-diphenyl acetate (Compound 15);

(2R,2S) (1α,5α,6α)-N-[3-azabicyclo[3.1.0]hexyl-6-(aminomethyl)-yl]-2-hydroxy-2,2-diphenyl acetamide (Compound 16);

(2R,2S) (1α,5α,6α)-N-[3-azabicyclo[3.1.0]hexyl-6-(aminomethyl)-yl]-2-hydroxy-2-cyclohexyl-2-phenyl acetamide (Compound 17) and (2R,2S) (1α,5α,6α)-N-[3-azabicyclo[3.1.0]hex-6-yl methyl)-2-cyclopentyl-2-hydroxy-N-methyl-2-phenyl acetamide (Compound 18).

TABLE I

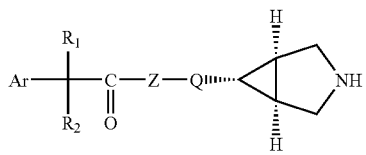

Formula III
(Formula I, wherein W = (CH$_2$)p where p = 0, X is no atom and Y = (CH$_2$)q, where q = 0, R$_6$ = R$_7$ = H)

| Compound No. | Ar | R$_1$ | R$_2$ | Z | Q |
|---|---|---|---|---|---|
| 1. (2R, 2S) | —C$_6$H$_5$ | —OH | cyclopentyl | NH— | —CH$_2$— |
| 2. (HCl salt) (2R, 2S) | —C$_6$H$_5$ | —OH | cyclopentyl | NH— | —CH$_2$— |
| 3. (2R) | —C$_6$H$_5$ | —OH | cyclopentyl | NH— | —CH$_2$— |
| 4. (HCl salt) (2R) | —C$_6$H$_5$ | —OH | cyclopentyl | NH— | —CH$_2$— |
| 5. (2S) | —C$_6$H$_5$ | —OH | cyclopentyl | NH— | —CH$_2$— |
| 6. (HCl salt) (2S) | —C$_6$H$_5$ | —OH | cyclopentyl | NH— | —CH$_2$— |
| 7. (2R, 2S) | —C$_6$H$_5$ | —OCH$_3$ | cyclopentyl | NH— | —CH$_2$— |
| 8. (2R, 2S) | —C$_6$H$_5$ | —OH | cycloheptyl | NH— | —CH$_2$— |
| 9. (2R, 2S) | —C$_6$H$_5$ | —OH | cyclobutyl | NH— | —CH$_2$— |
| 10. (2R, 2S) Tartarate salt | —C$_6$H$_5$ | —OH | cyclobutyl | NH— | —CH$_2$— |
| 11. (2R) | —C$_6$H$_5$ | —OH | 3,3-difluoro cyclopentyl | NH— | —CH$_2$— |
| 12. (2R, 2S) | —C$_6$H$_5$ | —OH | 3-fluoro cyclopentyl | NH— | —CH$_2$— |
| 13. (2R, 2S) | —C$_6$H$_5$ | —OH | 3,3-difluoro cyclopentyl | NH— | —CH$_2$— |
| 14. (2R, 2S) Tartarate salt | —C$_6$H$_5$ | —OH | 3,3-difluoro cyclopentyl | NH— | —CH$_2$— |
| 15. (2R, 2S) | —C$_6$H$_5$ | —OH | phenyl | O | —CH$_2$— |
| 16. (2R, 2S) | —C$_6$H$_5$ | —OH | phenyl | NH— | —CH$_2$— |
| 17. (2R, 2S) | —C$_6$H$_5$ | —OH | cyclohexyl | NH— | —CH$_2$— |
| 18. (2R, 2S) | —C$_6$H$_5$ | —OH | cyclopentyl | —N—CH$_3$ | —CH$_2$— |
| 19. | p-F—C$_6$H$_4$ | —F | —C$_6$H$_5$ | NH— | —CH(OH)— |
| 20. | o-Cl-p-F—C$_6$H$_3$ | —NH$_2$ | 1-cyclohexenyl | —O— | —CH(OH)— |
| 21. | 3-pyrrolyl | —Cl | p-CH$_3$—C$_6$H$_4$ | —O— | —CH(CH$_3$)— |
| 22. | 3-pyridyl | CH$_2$(OH) | Cyclobutyl | —O— | —CH(OH)— |
| 23. | 3-furyl | —F | —C$_6$H$_5$ | N(CH$_3$) | —CH$_2$CH$_2$— |
| 24. | 1-indolyl | —Cl | Cyclohexyl | —S— | —CH$_2$— |
| 25. | 3-isothiazolyl | —F | —C$_6$H$_5$ | —NH— | —CH(OH)— |
| 26. | 3-isoxazolyl | N(CH$_3$)$_2$ | o-Cl-p-F—C$_6$H$_3$ | —O— | —CH$_2$CH$_2$— |

Because of their valuable pharmacological properties, the compounds described herein may be administered to an animal for treatment orally, or by a parenteral route. The pharmaceutical compositions described herein can be produced and administered in dosage units, each unit containing a certain amount of at least one compound described herein and/or at least one physiologically acceptable addition salt thereof. The dosage may be varied over extremely wide limits as the compounds are effective at low dosage levels and relatively free of toxicity. The compounds may be administered in the low micromolar concentration, which is therapeutically effective, and the dosage may be increased as desired up to the maximum dosage tolerated by the patient.

The compounds described herein can be produced and formulated as their enantiomers, diastereomers, N-Oxides, polymorphs, solvates and pharmaceutically acceptable salts, as well as metabolites having the same type of activity. Pharmaceutical compositions comprising the molecules of Formulae I, II, III, IV and V or metabolites, enantiomers, diastereomers, N-oxides, polymorphs, solvates or pharmaceutically acceptable salts thereof, in combination with pharmaceutically acceptable carrier and optionally included excipient can also be produced.

Compounds such as those described in Table I, for example, can be prepared from the appropriate acetic acid, in analogy to specific examples provided below. The preparation of such acetic acids is known to those of ordinary skill in the art, and will be recognized by reference to the cited specific examples given below. Other compounds within the scope of the invention, such as those having $R_6$ and/or $R_7$ as methyl, carboxylic acid, amide, amino or methylamino will be readily prepared in analogy to the specific procedures given in the specific examples below, using appropriate azabicylo[3.1.0]hexanes which are synthesized using known methods. Other compounds within the scope of the invention, such as those having X as oxygen, sulfur or secondary or tertiary amine can be prepared in analogy to the specific procedures given in the specific examples below, using appropriate esters, thiocompounds, or amides which can be made by procedures known to those of ordinary skill in the art. Similarly, compounds within the scope of the invention, such as those having Y as $CHR_5CO$ where $R_5$ is hydrogen or methyl can be made in analogy to the specific procedures given in the specific examples below, using appropriate anhydrides, imides or thioanhydrides which are made by procedures known to those of skill in the art. Other compounds within the scope of the invention, such as those having Z as oxygen, sulfur or secondary or tertiary amino can be made in analogy to the specific procedures given in the specific examples below, using appropriate starting materials which are made by procedures known to those of ordinary skill in the art.

The examples mentioned below demonstrate general synthetic procedures, as well as specific preparations of particular compounds. The examples are provided to illustrate the details of the invention and should not be constrained to limit the scope of the present invention.

EXAMPLES

Various solvents, such as acetone, methanol, pyridine, ether, tetrahydrofuran, hexanes, and dichloromethane, were dried using various drying reagents according to procedures described in the literature. IR spectra were recorded as nujol mulls or a thin neat film on a Perkin Elmer Paragon instrument, Nuclear Magnetic Resonance (NMR) were recorded on a Varian XL-300 MHz instrument using tetramethylsilane as an internal standard.

Example 1

Preparation of (2R,2S) (1α,5α,6α)-N-[3-azabicyclo [3.1.0]hexyl-6-(aminomethyl)-yl]-2-hydroxy-2-cyclopentyl-2-phenyl acetamide (Compound No. 1)

Step a: Synthesis of (2R,2S) (1α,5α,6α)-N-[3-benzyl 3-azabicyclo[3.1.0]hexyl-6-(aminomethyl)-yl]-2-hydroxy-2-cyclopentyl-2-phenyl acetamide To a solution of (1α,5α,6α)-6-aminomethyl-3-benzyl-3-azabicylo[3.1.0]hexane (prepared as described in EP 0413455 A2) (29.9 mmol, 6.05 gm) in dimethyl formamide (100 ml) was added 2-(R,S)-hydroxy-2-cyclopentyl-2-phenyl acetic acid (prepared following *J. Amer Chem. Soc.,* 1953; 75:2654) (27.2 mmol, 6.0 gm) and cooled to 0° C. The reaction mixture was treated with hydroxy benzotriazole (29.9 mmol, 4.04 gm) followed by N-methyl morpholine (54.4 mmol, 5.2 gm) was stirred at 0° C. for 0.5 hours. EDC (1-[3-(dimethylamino)propyl]-3-ethyl carbodiimide hydrochloride (29.9 mmol, 5.7 gins) was added and the reaction mixture was stirred at 0° C. for 1 hour and further at room temperature (RT) overnight. The reaction mixture was poured into saturated sodium bicarbonate and extracted with ethyl acetate. The organic layers were washed with water and dried over sodium sulphate and concentrated under reduced pressure. The residue was purified by column chromatography (silica gel 100-200 mesh) eluting compound in 93-95% purity. To obtain higher purity (about 99%) of the compound, it was triturated with toluene and filtered.

Step b: Preparation of (2R,2S) (1α,5α,6α)-N-[3-azabicyclo[3.1.0]hexyl-6-(aminomethyl)-yl]-2-hydroxy-2-cyclopentyl-2-phenyl acetamide To a solution of (2R,2S) (1α,5α,6α)-N-[3-benzyl-3-azabicyclo[3.1.0]hexyl-6-aminomethyl-yl]-2-hydroxy-2-cyclopentyl-2-phenyl acetamide from Example 1, step a (1.0 g, 2.48 mmol) in methanol (25.0 ml), 5% Pd—C (0.2 g), (50% wet) was added under $N_2$. Then, anhydrous ammonium formate (0.8 g, 12.38 mmol) was added under stirring and the reaction mixture was refluxed for half an hour under the $N_2$ atmosphere. The mixture was cooled to room temperature and the reaction mixture was filtered through a bed of hyflo. The hyflo bed was washed with methanol (75.0 ml), ethyl acetate (25.0 ml) and water (25.0 ml). The filtrate was concentrated under vaccum. The residue was diluted with water and pH of the resulting solution was adjusted to pH~14 with 1N NaOH. The solution was extracted with ethyl acetate (2×50 ml) and the ethyl acetate layer was washed with water and brine solution. The layer was dried over anhydrous $Na_2SO_4$ and concentrated to give the title compound as solid in 96.2% (0.75 g, 2.39 mmol) yield with >98% purity by HPLC.

The compound exhibited a melting point of 149-151° C., and had infrared absorbance (KBr) at 3410, 2951.5, 2868.3, and 1652.5 $cm^{-1}$. $^1HNMR$ ($CDCl_3$) spectral data were as follows: δ 7.59-7.62 (m, 2H), 7.23-7.36 (m, 3H), 6.56 (brs, 1H), 3.03-3.15 (m, 3H), 2.78-2.90 (m, 4H, including OH), 1.51-1.71 (m, 8H), 1.19-1.27 (m, 4H), 0.70-0.72 (m, 1H). The mass spectrum showed peaks at m/e of 315 ($MH^+$), 297 (M-OH).

Example 2

Preparation of (2R,2S) (1α,5α,6α)-N-[3-azabicyclo [3.1.0]hexyl-6-(aminomethyl)-yl]-2-hydroxy-2-cyclopentyl-2-phenyl acetamide. Hydrochloride salt (Compound No. 2)

To a solution of (2R,2S) (1α,5α,6α)-N-[3-azabicyclo [3.1.0]hexyl-6-(aminomethyl)-yl]-2-hydroxy-2-cyclopentyl-2-phenyl acetamide (prepared in Example 1) (0.2 g, 0.637 mmole) in dichloromethane (4.0 ml), ethanolic HCL (1.45 N, 0.5 ml, 0.725 mmol) was added at room temperature and stirred for 10 minutes. At the same temperature diethyl ether (100 ml) was added to the reaction mixture, stirred for 5 minutes and concentrated under vacuum without heating. The residue was triturated with ether to get solid material. The ether layer was decanted and the solid was dried under vacuum to get the title compound as a hygroscopic solid in 94% (0.21 g, 0.6 mmole) yield with >98% purity by HPLC.

Example 3

Preparation of (2R)-(1α,5α,6α)-N-[3-azabicyclo [3.1.0]hexyl-6-(aminomethyl)-yl]-2-hydroxy-2-cyclopentyl-2-phenyl acetamide (Compound No. 3)

Step a: Synthesis of (2R)-(1α,5α,6α)-N-[3-benzyl-3-azabicyclo[3.1.0]hexyl-6-(aminomethyl)-yl]-2-hydroxy-2-cyclopentyl-2-phenyl acetamide This compound was synthesised following the procedure of Example 1, Step a, using (2R)-2-hydroxy-2-cyclopentyl-2-phenyl acetic acid (synthesised as in Grover et. al., *J. Org. Chem.*, 2000; 65:6283-6287), instead of 2-hydroxy-2-cyclopentyl-2-phenyl acetic acid.

Step b: Synthesis of (2R)-(1α,5α,6α)-N-[3-azabicyclo[3.1.0]hexyl-6-(aminomethyl)-yl]-2-hydroxy-2-cyclopentyl-2-phenyl acetamide This compound was synthesised following the procedure of Example 1, Step b, using (2R)-(1α,5α,6α)-N-[3-benzyl-3-azabicyclo[3.1.0]hexyl-6(aminomethyl)-yl]-2-hydroxy-2-cyclopentyl-2-phenyl acetamide instead of (2R,2S) (1α,5α, 6α)-N-[3-benzyl-3-azabicyclo[3.1.0]hexyl-6-(aminomethyl)-yl]-2-hydroxy-2-cyclopentyl-2-phenyl acetamide. The enantiomeric excess (ee) was determined by HPLC (Chinacel OD, mobile phase 90% hexane/10% EtOH/ 0.1% TFA) by observing the (S) and (R) isomers. The (S) isomer elutef at approximately 11.11 min. The (R) isomer eluted at approximately 11.81 min. The optical purity was >99%.

The compound exhibited a melting point of 150.2° C. Infrared spectral data showed (DCM): 1653.8 cm$^{-1}$. $^1$HNMR spectral data showed (CDCl$_3$):δ 7.61 (d, J=9 Hz, 2H), 7.30-7.38 (m, 2H), 6.70 (s,1H), 3.61-3.68 (m, 2H), 3.08-3.28 (m, 5H), 1.49-1.68 (m, 10H), 1.11-1.26 (m, 2H), 0.75-0.85 (m, 1H).

Example 4

Preparation of (2R)-(1α,5α,6α)-N-[3-azabicyclo [3.1.0]hexyl-6-aminomethyl)-yl]-2-hydroxy-2-cyclopentyl-2-phenyl acetamide, hydrochloride salt (Compound No. 4)

The hydrochloride salt was synthesised following the same procedure as in Example 2, using (2R)-(1α,5α,6α)-N-[3-azabicylo[3.1.0]hexyl-6-(aminomethyl)-yl]-2-hydroxy-2-cyclopentyl-2-phenyl acetamide instead of (2R,2S) (1α,5α, 6α)-N-[3-azabicyclo[3.1.0]hexyl-6-(aminomethyl)-yl]-2-hydroxy-2-cyclopentyl-2-phenyl acetamide.

Example 5

Preparation of (2S)-(1α,5α,6α)-N-[3-azabicyclo [3.1.0]hexyl-6-(aminomethyl)-yl]-2-hydroxy-2-cyclopentyl-2-phenyl acetamide (Compound No. 5)

Step a: Synthesis of (2S)(1α,5α,6α)-N-[3-benzyl-3-azabicyclo[3.1.0]hexyl-6-(aminomethyl)-yl]-2-hydroxy-2-cyclopentyl-2-phenyl acetamide This compound was synthesized following the procedure of Example 1, Step a, using (2S)-2-hydroxy-2-cyclopentyl-2-phenyl acetic acid (synthesised as in Grover et. al., *J. Org. Chem.*, 2000; 65:6283-6287), instead of 2-hydroxy-2-cyclopentyl-2-phenyl acetic acid.

Step b: Synthesis of (2S)(1α,5α,6α)-N-[3-azabicyclo [3.1.0]hexyl-6-(aminomethyl)-yl]-2-hydroxy-2-cyclopentyl-2-phenyl acetamide This compound was synthesized following the procedure of Example 1, Step b, using (2S)-(1α,5α,6α)-N-[3-benzyl-3-azabicyclo[3.1.0]hexyl-6(aminomethyl)-yl]-2-hydroxy-2-cyclopentyl-2-phenyl acetamide instead of (2R,2S) (1α,5α, 6α)-N-[3-benzyl-3-azabicyclo[3.1.0]hexyl-6-(aminomethyl)-yl]-2-hydroxy-2-cyclopentyl-2-phenyl acetamide. The ee was determined by HPLC (Chinacel OD, mobile phase 90% hexane/10% EtOH/0.1% TFA) by observing the (S) and (R) isomers. The (S) isomer eluted at approximately 11.11 min. The (R) isomer eluted at approximately 11.81 min. The optical purity was >99%.

The compound exhibited a melting point of 62.6-63.3° C. Infrared spectral data showed (KBr): 1653.7 cm$^{-1}$. $^1$HNMR spectral data showed (CDCl$_3$): δ 7.59-7.62 (m, 2H), 7.29-7.37 (m, 3H), 3.58-3.65 (m, 2H), 3.02-3.24 (m, 4H), 1.11-1.34 (m, 11H), 0.75-0.95 (m, 1H).

Example 6

Preparation of (2S)-(1α,5α,6α)-N-[3-azabicyclo [3.1.0]hexyl-6-aminomethyl)-yl]-2-hydroxy-2-cyclopentyl-2-phenyl acetamide, hydrochloride salt (Compound No. 6)

The hydrochloride salt was synthesized in 90% yield following the procedure of Example 2, using (2S)-(1α,5α,6α)-N-[3-azabicylo[3.1.0]hexyl-6-(aminomethyl)-yl]-2-hydroxy-2-cyclopentyl-2-phenyl acetamide instead of (2R,2S) (1α,5α,6α)-N-3-azabicyclo[3.1.0]hexyl-6-(aminomethyl)-yl]-2-hydroxy-2-cyclopentyl-2-phenyl acetamide.

Example 7

Preparation of (2R,2S) (1α,5α,6α)-N-[3-azabicyclo [3.1.0]hexyl-6-(aminomethyl)-yl]-2-methoxy-2-cyclopentyl-2-phenyl acetamide (Compound 7)

Step a: Preparation of (2R,2S) 2-methoxy-2-cyclopentyl-2-phenyl acetic acid ethyl ester To a cold solution of (2R,2S) 2-hydroxy-2-cyclopentyl-2-phenyl acetic acid ethyl ester (synthesized as per *J. Am. Chem. Soc.*, 1953; 75:2654) (4.5 mmol) in dimethyl formamide was added sodium hydride (9.08 mmol) in portions at 0° C. and stirred at room temperature for 1 hr. Reaction mixture was cooled to 0° C. and iodomethane (18.0 mmol) was added. Reaction mixture was then stirred at room temperature for 2 hrs. TLC showed absence of starting material. Water was added to reaction mixture extracted with ethylacetate. The organic layer dried over anhydrous sodium sulfate and concentrated. Crude compound was purified by column chromatography & desired product eluted with 2% EtOAc/Hexane.

$^1$H NMR (CDCl$_3$)spectral data were as follows: δ 7.47-7.36 (5H, m), 4.31 (2H, q), 3.26 (3H, s), 2.43 (1H, m), 1.66-1.46 (11H, m)

Step b: Synthesis of (2R,2S) 2-methoxy-2-cyclopentyl-2-phenyl acetic acid

To a solution of (2R,2S) 2-methoxy-2-cyclopentyl-2-phenyl acetic acid ethyl ester (1.8 mmol) in methanol, potassium hydroxide (KOH) (2.2 mmol) was added and the reaction mixture refluxed for 7 hrs. TLC showed presence of starting material then 3 mole equivalent KOH was added and reaction mixture refluxed for 3 hrs. TLC showed absence of starting materials. Reaction mixture was concentrated, residue was taken in water and neutralized with concentrated hydrochloric acid & extracted with ethylacetate. Organic layer was washed with water, brine, dried over anhydrous sodium sulphate and concentrated under reduced pressure to obtain the desired compound.

$^1$H NMR (CDCl$_3$)spectral data were as follows: δ 7.48-7.35 (5H, m), 3.20 (3H, s), 2.94-2.86 (1H, m), 1.86-1.50 (8H, m)

Step c: Preparation of (2R,2S) (1α,5α,6α)-N-[3-benzyl-3-azabicyclo[3.1.0] hexyl-6-(aminomethyl)-yl]-2-methoxy-2-cyclopentyl-2-phenyl acetamide This was prepared following the procedure of Example 1, step 'a' by using 2-methoxy-2-cyclopentyl-2-phenyl acetic acid instead of 2-hydroxy-2-cyclopentyl-2-phenyl acetic acid.

Step d: Preparation of (2R,2S) (1α,5α,6α)-N-[3-azabicyclo[3.1.0]hexyl-6-(aminomethyl)-yl]-2-methoxy-2-cyclopentyl-2-phenyl acetamide This was prepared following the procedure of Example 1, step b by using (2R,2S) (1α,5α,6α)-N-[3-azabicyclo[3.1.0]hexyl-6-(aminomethyl)-yl]-2-methoxy-2-cyclopentyl-2-phenyl acetamide instead of (2R,2S) (1α,5α,6α)-N-[3-benzyl-3-azabicyclo[3.1.0]hexyl-6-(aminomethyl)-yl]-2-hydroxy-2-cyclopentyl-2-phenyl acetamide $^1$H NMR (CDCl$_3$)spectral data showed: δ 7.45-7.30 (5H, m), 7.03 (1H, m), 3.25-3.02 (9H, m), 2.00-0.86 (12H, m).

Example 8

Preparation of (2R,2S) (1α,5α,6α)-N-[3-azabicyclo [3.1.0]hexyl-6-(aminomethyl)-yl]-2-hydroxy-2-cycloheptyl-2-phenyl acetamide (Compound 8)

Step a: Synthesis of (2R,2S)(1α,5α,6α)-N-[3-benzyl-3-azabicyclo[3.1.0]hexyl-6-(aminomethyl)-yl]-2-hydroxy-2-cycloheptyl-2-phenyl acetamide This compound was synthesized following the procedure of Example 1, step a, using (2R,2S)-2-hydroxy-2-cycloheptyl-2-phenyl acetic acid (synthesized as in Grover et. al., *J. Org. Chem*, 2000; 65:6283-6287), instead of 2-hydroxy-2-cyclopentyl-2-phenyl acetic acid.

Step b: Synthesis of (2R,2S) (1α,5α,6α)-N-[3-azabicyclo[3.1.0]hexyl-6-(aminomethyl)-yl]-2-hydroxy-2-cycloheptyl-2-phenyl acetamide This compound was synthesized following the procedure of Example 1, step b, using (2R,2S)—(1α,5α,6α)-N-[3-benzyl-3-azabicyclo[3.1.0]hexyl-6-(aminomethyl)-yl]-2-hydroxy-2-cycloheptyl-2-phenyl acetamide instead of (2R,2S) (1α,5α,6α)-N-[3-benzyl-3-azabicyclo[0.1.0]hexyl-6-(aminomethyl)-yl]-2-hydroxy-2-cyclopentyl-2-phenyl acetamide in 90% yield.

The compound had $^1$H NMR spectral data showed (CDCl$_3$):δ 7.59-7.61 (m, 2H), 7.13-7.36 (m, 3H), 6.76 (brs, 1H), 3.00-3.20 (m, 2H), 2.80-2.92 (m, 2H), 2.50-2.80 (m, 1H), 2.40 (brs, 2H), 1.28-1.73 (m, 12H), 1.00-1.20 (m, 2H), 0.80-0.90 (m, 1H).

Infrared absorbence (DCM) at 1655.7 cm$^{-1}$

The mass spectrum showed peaks at m/e of: 343 (MH$^+$)

Example 9

Preparation of (2R,2S) (1α,5α,6α)-N-[3-azabicyclo [3.1.0]hexyl-6-(aminomethyl)-yl]-2-hydroxy-2-cyclobutyl-2-phenyl acetamide (Compound 9)

Step a: synthesis of (2R,2S) (1α,5α,6α)-N-[3-benzyl-3-azabicyclo[3.1.0]hexyl-6-(aminomethyl)-yl]-2-hydroxy-2-cyclobutyl-2-phenyl acetamide This compound was synthesized following the procedure of Example 1, step a, using (2R,2S) 2-hydroxy-2-cyclobutyl-2-phenyl acetic acid (synthesized as per reported procedure of Saul B. Kadin and Joseph G. Cannon., *J. Org. Chem.*, 1962; 27:240-245), instead of 2-hydroxy-2-cyclopentyl-2-phenyl acetic acid.

Step b: Synthesis of (2R,2S) (1α,5α,6α)-N-[3-azabicyclo[3.1.0]hexyl-6-(aminomethyl)-yl]-2-hydroxy-2-cyclobutyl-2-phenyl acetamide This compound was synthesized following the procedure of Example 1, step b, using (2R,2S) (1α,5α,6α)-N-[3-benzyl-3-azabicyclo[3.1.0]hexyl-6-(aminomethyl)-yl]-2-hydroxy-2-cyclobutyl-2-phenyl acetamide instead of (2R,2S) (1α,5α,6α)-N-[3-benzyl-3-azabicyclo[3.1.0]hexyl-6-(aminomethyl)-yl]-2-hydroxy-2-cyclopentyl-2-phenyl acetamide to give the title compound with 90.6% purity by HPLC.

$^1$HNMR (CDCl$_3$) spectral data were as follows: δ 7.50 (2H, m), 7.30 (3H, m), 6.60 (1H, m), 3.60-3.00 (9H, m), 2.04 (1H, m), 1.96-1.74 (6H, m), 1.45 (1H, m), 1.00 (1H, m).

Example 10

Preparation of (2R,2S) (1α,5α,6α)-N-[3-azabicyclo [3.1.0]hexyl-6-(aminomethyl)-yl]-2-hydroxy-2-cyclobutyl-2-phenyl acetamide tartarate salt (Compound 10)

To a solution of compound No. 9 in ethanol, solid tartaric acid was added and the solution was stirred for 1 hour at room temperature and the solvent was evaporated. Ether was added to it to precipitate the salt. It was washed with ether (4 times) by decanting supernatant liquid to give the salt as powder with 95.66% purity by HPLC.

$^1$H NMR (CDCl$_3$) spectral data were as follows: δ 7.45 (2H, m), 7.21 (3H, m), 4.36 (2H, s), 3.42 (2H, m), 3.20 (3H, m), 3.05 (2H, m), 1.97 (1H, m), 1.90-1.60 (7H, m), 1.10 (1H, m).

Example 11

Preparation of (2R) (1α,5α,6α)-N-[3-azabicyclo [3.1.0]hexyl-6-(aminomethyl)-yl]-2-hydroxy-2-(3,3-difluoro cyclopentyl)-2-phenyl acetamide (Compound 11)

Step a: Preparation of (2R,5R)-2-tert-butyl-5-phenyl-1,3-dioxalan-4-one

The compound was synthesised following the procedure described in *J. Org. Chem.*, 2000; 65:6283-6287.

Step b: Preparation of (2R,5R)-2-tert-butyl-5-[(1R or 1S)-3-oxocyclopentyl]-5-phenyl-1,3-dioxalan-4-one To a suspension of compound of step a (1.36 mmol) in tetrahydrofuran (THF) (12 ml) was added lithium diisopropyl amide (LDA) in THF (1.5 mmol) drop wise at −78° C. under nitrogen atmosphere. The reaction mixture was stirred at the same temperature for 2 hours. A solution of 2-cyclopenten-1-one (1.52 mmol) in THF (2 ml) was added to the reaction mixture dropwise and stirred for additional 3 hours. The reaction mixture was quenched with saturated aq.ammonium chloride solution and extracted with ethyl acetate. The organic layer was dried and the residue obtained after removing the solvents in vacuo was purified by column chromatography (100-200 mesh silica gel). The product was eluted with 10% EtOAc-hexane mixture.

$^1$HNMR(CDCl$_3$): δ-values: 7.70-7.26 (m,5Ar—H), 5.43-5.37 (d, 1H), 2.91-2.88 (m, 1H), 2.37-1.77 (m,6H), 0.92 (s, 9H)

IR(DCM): 1791 and 1746 cm$^{-1}$

Step c: Preparation of (2R,5R)-2-tert-butyl-5-[(1R or 1S)-3,3-difluorocyclopentyl]-5-phenyl-1,3-dioxalan-4-one To a solution of compound of step-b (1 mmol) in chloroform (15 ml) was added diethylamino sulphurtrifluoride (DAST), (3.3 mmol) at 0° C. under nitrogen atmosphere. The reaction mixture was stirred at the same temperature for 30 minutes and then at room temperature for 3 days. After being cooled to 0° C., the reaction mixture (RM) was quenched carefully by adding water. The organic layer was separated and the aqueous layer extracted with chloroform. The combined organic layers were dried and the residue obtained after removing the solvent was purified by column chromatography (100-200 mesh size silica gel) eluting the compound with 5% EtOAc-hexane mixture.

$^1$HNMR(CDCl$_3$): δ-values: 7.73-7.35 (m,5Ar—H), 5.49 (s,1H), 2.86-2.82 (m,1H), 2.27-1.80 (m,6H), 0.98 (s,H)

IR(DCM): 1793 cm$^{-1}$

Step d: Preparation of (2R)-[(1S or 1R)-3,3-difluorocyclopentyl]-2-hydroxy-2-phenylaceticacid The solution of compound of step-c (1 mmol) in MeOH (10 ml) was stirred with 3N aqueous sodium hydroxide solution for overnight at room temperature. The reaction mixture was concentrated under reduced pressure. The residue was diluted with water and extracted with dichloromethane. The aqueous layer was acidified with conc.hydrochloric acid and extracted with EtOAc. The organic layer was dried and concentrated under reduced pressure to give the product.

m.pt.:123° C.

$^1$HNMR(CDCl$_3$): δ-values: 7.69-7.37(m,5Ar—H), 3.29-3.20(m,1H), 2.39-1.68 (m,6H)

Step e: Preparation of (1α,5α,6α)-6-aminomethyl-3-benzyl-3-azabicyclo[3.1.0]hexane.

The compound was synthesised as per the procedure of EP 0413455A2.

Step f: Preparation of (2R)-(1α,5α,6α)-N-[3-benzyl-3-azabicyclo[3.1.0]hexyl-6-(aminomethyl)-yl]-2-[(1R or 1S)-3,3-difluorocyclopentyl]-2-hydroxy-2-phenylacetamide It was prepared following the procedure of Example 1, step a, using the acid synthesized in step d instead of 2-hydroxy-2-cyclopentyl-2-phenyl acetic acid.

Step g: Synthesis of (2R) (1α,5α,6α)-N-[3-azabicyclo[3.1.0]hexyl-6-(aminomethyl)-yl]-2-hydroxy-2-(3,3-difluorocyclopentyl)-2-phenyl acetamide It was prepared by following the procedure of Example 1, step b by using (2R) (1α,5α,6α)-N-[3-benzyl-3-azabicyclo[3.1.0]hexyl-6-(aminomethyl)-yl]-2-hydroxy-2-(3,3-difluorocyclopentyl)-2-phenyl acetamide instead of (2R,2S) (1α,5α,6α)-N-[3-benzyl-3-azabicyclo[3.1.0]hexyl-6-(aminomethyl)-yl]-2-hydroxy-2-cyclopentyl-2-phenyl acetamide. The optical purity is 87.27% (HPLC).

$^1$H NMR (CDCl$_3$) spectral data showed: δ 7.59-7.55 (2H, m), 7.35-7.31 (3H, m), 7.03 (1H, m), 3.18-3.11 (7H, m), 1.87-1.62 (9H, m).

Example 12

Preparation of (2R,2S) (1α,5α,6α)-N-[3-azabicyclo[3.1.0]hexyl-6-(aminomethyl)-yl]-2-hydroxy-2-(3-fluorocyclopentyl)-2-phenyl acetamide (Compound 12)

Step-a: Preparation of (2R,2S)-2-tert-butyl-5-[(1R or 1S, 3R or 3S)-3-hydroxy cyclopentyl]-5-phenyl-1,3-dioxalan-4-one To a solution of (2R,2S,5R)-2-tert-butyl-5-[(1R or 1S]-3-oxocyclopentyl]-5-phenyl-1,3-dioxalan-4-one (1 mmol) in methanol (10 ml) cooled to 0° C., sodium borohydride (2 mmol) was added in small lots with stirring. The RM was stirred at 0° C. for 1 hr. It was concentrated under reduced pressure and the residue diluted with water and extracted with EtOAc. The organic layer was dried and the residue obtained after the removal of solvents was purified by column chromatography (100-200 mesh silica gel) eluting the compound with 20% EtOAc-hexane mixture.

$^1$HNMR(CDCl$_3$): δ-values: 7.68-7.29 (m, 5H, ArH), 5.45 (d,1H), 4.30 (m, 1H), 3.25 (m, 1H), 2.65-2.63 (m, 1H), 1.80-1.63 (m, 6H), 0.92 (s, 9H)

IR(DCM): 1789 cm$^{-1}$, 3386 cm$^{-1}$

Step-b: Preparation of (2R,2S)-2-tert-butyl-5-[1R or 1S, 3R or 3S]-3-fluorocyclopentyl]-5-phenyl-1,3-dioxolan-4-one The solution of compound of step-a (1 mmol) in chloroform (10 ml) was cooled to 0° C. and diethylamino sulphur trifluoride (DAST) (1.5 mmol) was added dropwise under nitrogen atmosphere. The RM was stirred at 0° C. for 30 minutes and then at room temperature for 3 days. The RM was cooled and carefully quenched with aqueous ammonium chloride solution. The organic layer was separated and aqueous layer extracted with EtOAc. The combined organic layer was dried and residue obtained after removing the solvents was purified by column chromatography (100-200 mesh, silica gel) eluting the compound with 5% EtOAc-hexane mixture.

$^1$HNMR(CDCl$_3$): δ-values: 7.68-7.28 (m, 5H, Ar—H), 5.46 (d,1H), 5.39 (m, 1H), 2.90 (m, 1H), 1.98-1.25 (m, 6H), 0.93 (s, 9H)

Step-c: Preparation of (2R,2S)-[(1R or 1S, 3R or 3S]-3-fluorocyclopentyl]-2-hydroxy-2-phenylacetic acid The compound was synthesised following the procedure of Example 11, step-d using (2R,2S,5R)-2-tert-butyl-5-[(1R or 1S, 3R or 3S)-3-fluorocyclopentyl]-5-phenyl-1,3-dioxolan-4-one instead of (2R,5R)-2-tert-butyl-5-[(1R or 1S)-3,3-difluorocyclopentyl]-5-phenyl-1,3-dioxolan-4-one.

$^1$HNMR(CDCl$_3$): δ 7.66-7.27 (m, 5Ar—H), 5.30-5.00 (m, H), 3.32-3.16 (m, 1H), 2.05-1.26 (m, 6H).
IR(DCM): 1710 cm$^{-1}$

Step-d: Preparation of (2R,2S)-(1α,5α,6α)-N-[3-benzyl-3-azabicyclo[3.1.0]hexyl-6-(aminomethyl)-yl]-2-[1R or 1S, 3R or 3S]-3-fluorocyclopentyl]-2-hydroxy-2-phenylacetamide This compound was synthesized following the procedure of Example 1, step a, using the acid synthesized in the above step-c, instead of 2-hydroxy-2-cyclopentyl-2-phenyl acetic acid.

Step-e: Preparation of (2R,2S)(1α,5α,6α)-N-[3-azabicyclo[3.1.0]hexyl-6-(aminomethyl)-yl]-2-hydroxy-2-(3-fluorocyclopentyl)-2-phenyl acetamide This compound was synthesized following the procedure of Example 1, step b, using (2R,2S)-(1α,5α,6α)-N-[3-benzyl-3-azabicyclo[3.1.0]hexyl-6-(aminomethyl)-yl]-2-[1R or 1S, 3R or 3S]-3-fluorocyclopentyl]-2-hydroxy-2-phenylacetamide instead of (2R,2S) (1α,5α,6α)-N-[3-benzyl-3-azabicyclo[3.1.0]hexyl-6-(aminomethyl)-yl]-2-hydroxy-2-cyclopentyl-2-phenyl acetamide. The optical purity was 87.27% (HPLC).

$^1$H NMR spectral data showed (CDCl$_3$): δ 7.56 (2H, m), 7.35 (3H, m), 6.08 (1H, m), 5.30-5.03 (1H, m), 3.27 (1H, m), 3.11 (2H, m), 2.91 (4H, m), 2.04-1.48 (9H, m), 0.71 (1H, m).

Example 13

Preparation of (2R,2S) (1α,5α,6α)-N-[3-azabicyclo[3.1.0]hexyl-6-(aminomethyl)-yl]-2-hydroxy-2-(3,3-difluoro cyclopentyl)-2-phenyl acetamide (Compound 13)

This compound was prepared following the procedure of Example 11, by using (2R,2S) [(1α,5α,6α)-N-[3-benzyl-3-azabicyclo[3.1.0]hexyl-6-(aminomethyl)-yl]-2-hydroxy-2-(3,3-difluorocyclo-pentyl)-2-phenyl acetamide]instead of (2R) [(1α,5α,6α)-N-[3-benzyl-3-azabicyclo[3.1.0]hexyl-6-(aminomethyl)-yl]-2-hydroxy-2-(3,3-difluorocyclo-pentyl)-2-phenyl acetamide] in step g, Example 11.

The optical purity is 83.778% (HPLC).
$^1$H NMR spectral data showed (CDCl$_3$)δ: 7.57-7.30 (5H, m), 6.49-6.44 (1H, m), 3.33 (1H, m), 3.10 (2H, m), 6.49-6.44 (1H, m), 3.33 (1H, m), 3.10 (2H, m), 2.87 (3H, m), 2.23-1.80 (8H, m), 1.79-1.20 (2H, m)
IR (KBr): 3410,1654 cm$^{-1}$

Example 14

Preparation of (2R,2S) (1α,5α,6α)-N-[3-azabicyclo[3.1.0]hexyl-6-(aminomethyl)-yl]-2-hydroxy-2-(3,3-difluorocyclopentyl)-2-phenyl acetamide tartarate salt (Compound 14)

To a solution of compound No. 13 in ethanol was added tartaric acid & heated the reaction mixture at 60° C. for 1 hour. The reaction mixture was then concentrated under reduced pressure, added diethyl ether and the organic layer was removed to get light brown solid as the desired compound. The optical purity was found to be 98.14% (HPLC)

$^1$H NMR spectral data showed (CD$_3$OD): δ 7.50 (2H, m), 7.20 (3, m), 4.40 (2H, s), 3.60-3.00 (6H, m), 2.10-1.60 (8H, m), 1.19 (1H, m), 0.90 (1H, m).
IR (KBr): 3407, 1653 cm$^{-1}$

Example 15

Preparation of (2R,2S) (1α,5α,6α)-N-[3-azabicyclo[3.1.0]hexyl-6-(methyl)-yl]-2-hydroxy-2,2-diphenyl acetate (Compound 15)

Step a: Synthesis of (2R,2S) (1α,5α,6α)-N-[3-benzyl-3-azabicyclo[3.1.0]hexyl-6-(methyl)-yl]-2-hydroxy-2,2-diphenyl acetate.

Step (i): Preparation of (1α,5α,6α)-3-benzyl-6-hydroxymethyl-3-azabicyclo[3.1.0]hexane.

Synthesized as per reported procedure of EP 0 413 455 A2

Step (ii): Preparation of (1α,5α,6α)-3-benzyl-6-(methanesulfonyloxy)methyl-3-azabicyclo[3.1.0]hexane:

A solution of the title compound of preparation of step (i) (0.203 g; 1 mmol) and triethyl amine (0.21 gms, 2 mmol) in ethyl acetate (25 ml) was cooled to −10° C. and treated with methanesulfonyl chloride (0.17 gms, 1.5 mmol). After stirring for one hour at −10° C., the reaction was poured into a saturated aqueous sodium bicarbonate solution. The organic layer was died over sodium sulphate. Filtration and removal of solvent in vacuo provided the title compound as a yellow oil, which was used as such in the following step without further purification.

$^1$H NMR (CDCl$_3$): δ-values: 7.45 (m, 5H, arom.), 4.29 (s, 2H), 3.81 (m, 2H), 3.13 (m, 4H), 2.84 (s, 3H), 1.38 (m, 3H)

Step (iii): Preparation of (1α,5α,6α)-[3-benzyl-3-azabicyclo[3.1.0]hexyl-6-(methyl)-yl]-2-hydroxy-2,2-diphenyl acetate To a solution of 2-hydroxy-2,2-diphenyl acetic acid (synthesized as per reported procedures in Vogel's textbook of "Practical Organic Chemistry," page 1046 (5' Ed); J. Am. Chem. Soc., 1953; 75:2654 and EP 613232) (1 mmol, 0.228 gms) in xylene was added, (1α,5α,6α)-3-benzyl-6-(methanesulfonyloxyl) methyl-3-azabicyclo[3.1.0]hexane (0.28 gms, 1 mmol) followed by DBU (1,8-diazabicyclo[5,4,0] undec-7-ene, (2 mmol, 0.305 gms) and the reaction mixture refluxed for 6 hrs. The RM was then washed with water, brine and dried over sodium sulphate. The solvents were evaporated and the crude compound thus obtained was purified by column chromatography (silicagel, 100-200 mesh) eluting the compound with 20-80, ethylacetate hexane.

$^1$H NMR (CDCl$_3$): δ-values: 7.46-7.22 (m, 15H, arom), 4.24 (s, 1H), 4.11-4.09 (d, 2H), 3.56 (s, 2H), 2.91-2.89 (d, 2H), 2.31-2.29 (d, 2H), 1.67-1.62 (m, 1H), 1.3 (s, 2H)
IR(DCM): 1724 cm$^{-1}$ Step b: Synthesis of (2R,2S) (1α,5α,6α)-N-[3-azabicyclo[3.1.0]hexyl (methyl)-yl]-2-hydroxy-2,2-diphenyl acetate It was debenzylated by following the procedure of Example 1, step b to give the title compound in 60% yield.

IR (KBr): 1731.6 cm$^{-1}$ $^1$H NMR (CDCl$_3$) spectral data showed: δ 7.33-7.47 (m, 10H), 4.17 (d, 2H, J=6 Hz), 2.72-2.92 (m, 4H), 0.94-0.99 (m, 2H), 0.88 (t, 1H), The mass spectrum showed peaks at m/e of 324 (M+1)

Example 16

Preparation of (2R,2S) (1α,5α,6α)-N-[3-azabicyclo[3.1.0]hexyl-6-(aminomethyl)-yl]-2-hydroxy-2,2-diphenyl acetamide (Compound 16)

Step a: Preparation of (2R,2S) (1α,5α,6α)-N-[3-benzyl-3-azabicyclo[3.1.0]hexyl-6-(aminomethyl)-yl]-2-hydroxy-2,2-diphenyl acetamide.

It was prepared following the procedure of Example 1, step a by using 2-hydroxy-2,2-diphenyl acetic acid (synthesized as per reported procedures in Vogel's textbook of "Practical Organic Chemistry," page 1046 (5$^{th}$ Ed), *J. Am. Chem. Soc.*, 1953; 75:2654 and EP 613232) instead of 2-hydroxy-2-cyclopentyl-2-phenyl acetic acid.

Step b: Preparation of (2R,2S) (1α,5α,6α)-[3-azabicyclo[3.1.0]hexyl-6-(aminomethyl)-yl]-2-hydroxy-2-(3,3-difluorocyclopentyl)-2-phenyl acetamide This compound was prepared following the procedure of Example 1, step b, using (1α,5α,6α)-N-[3-benzyl-3-azabicyclo[3.1.0]hexyl-6-(aminomethyl)-yl]-2-hydroxy-2,2-diphenylacetamide instead of (2R,2S) (1α,5α,6α)-N-[3-benzyl-3-azabicyclo[3.1.0]hexyl-6-(aminomethyl)-yl]-2-hydroxy-2-cyclopentyl-2-phenyl acetamide to give the title compound in 70% yield.

IR (KBr): 1658.0 cm$^{-1}$ $^1$H NMR (CDCl$_3$) spectral data showed: δ 7.34-7.44 (m, 10H), 6.53 (s, 1H), 3.17-3.26 (m, 2H), 2.87-3.01 (m, 4H), 1.38 (s, 2H), 0.88 (t, 1H).

The mass spectra showed peaks at m/e 323 (M+1), 305 (M-OH).

Example 17

Preparation of (2R,2S) (1α,5α,6α)-N-[3-azabicyclo[3.1.0]hexyl-6-(aminomethyl)-yl]-2-hydroxy-2-cyclohexyl-2-phenyl acetamide (Compound 17)

Step a: Synthesis of (1α,5α,6α)-N-[3-benzyl-3-azabicyclo[3.1.0]hexyl-6-(aminomethyl)-yl]-2-hydroxy-2-cyclohexyl-2-phenyl acetamide It was prepared following the procedure of Example 1, step a by using 2-hydroxy-2-cyclohexyl-2-phenyl acetic acid (synthesized as per the procedure described in *J. Amer. Chem. Soc.*, 1953; 75:2654) instead of 2-hydroxy-2-cyclopentyl-2-phenyl acetic acid.

Step b: Preparation of (2R,2S)(1α,5α,6α)-N-[3-azabicyclo[3.1.0]hexyl-6-(aminomethyl)-yl]-2-cyclohexyl-2-phenyl acetamide This compound was prepared following the procedure of Example 1, step b using (2R,2S) (1α,5α,6α)-N-[3-benzyl-3-azabicyclo[3.1.0]hexyl(aminomethyl)-yl]-2-hydroxy-2-cyclohexyl-2-phenyl acetamide instead of (2R,2S) (1α,5α,6α)-N-[3-benzyl-3-azabicyclo[3.1.0]hexyl-6-(aminomethyl)-yl]-2-hydroxy-2-cyclopentyl-2-phenyl acetamide to give the title compound in 80% yield.

IR (KBr): 1654.7 cm$^{-1}$ $^1$H NMR (CDCl$_3$) spectral data showed: δ 7.59-7.62 (m, 2H), 7.29-7.37 (m, 3H), 6.71 (s, 1H), 3.03-3.14 (m, 2H), 2.80-2.92 (m, 4H), 2.42 (m, 1H), 1.13-1.35 (m, 12H), 0.88 (m, 1H)

The mass spectra recorded peaks of 329 (M+1), 311 (M-OH).

Example 18

Preparation of (2R,2S) (1α,5α,6α)-N-[3-azabicyclo[3.1.0]hex-6-yl methyl)-2-cyclopentyl-2-hydroxy-N-methyl-2-phenyl acetamide (Compound 18)

Step a: Preparation of (2R,2S) (1α,5α,6α)-N-[3-tert-butyloxycarbonyl-3-azabicyclo[3.1.0]-hexyl-6-yl methyl]-2-hydroxy-2-cyclopentyl-2-phenyl acetamide To a solution of (1α,5α,6α)-3N-benzyl-6-amino-3-azabicyclo[3.1.0] hexane (synthesized as per reported procedure of Braish T. F. et. al., *Synlett.* 1996; 1100) (2.5 g, 7.96 mole) in (50.0 mmol) at 0° C., triethylamine (3.9 ml, 28 mmol) and Boc-anhydride (5.2 g, 23.9 mmol) were added. The reaction mixture was stirred at 0° C. for 30 minute and at room temperature for 12 hrs. Diluted with dichloromethane (50 ml) and washed with water and brine solution. Dried over anhydrous sodium sulfate and concentrated. The residue was purified by column chromatography using 25% ethyl acetate in hexane to give the title compound as solid in 86% (2.85 g, 6.9 mmol) yield. The compound exhibited a melting point of 179.5-182.9° C.

Step b: Preparation of (2R,2S) (1α,5α,6α)-N-[3-tert-butyloxycarbonyl-3-azabicyclo[3.1.0]hexyl-6-yl methyl)-2-(3-silyltrimethyloxy)-2-cyclopentyl-2-phenyl acetamide To a solution of Boc-derivative (2.0 g, 4.8 mmol) in dimethylformamide (10.0 ml), imidazole (1.2 g, 16.9 mmol) and trimethylsilyl chloride (1.54 ml, 12.0 mmol) were added and the reaction mixture was stirred at RT for 12 hrs. Diluted with water (50.0 ml) and extracted with ethyl acetate. The ethyl acetate layer was washed with water and brine solution. Dried and concentrated. The residue was purified by column chromatography using 15% ethyl acetate in hexane to give the title compound in 85% (2.0 g, 4.1 mmol) yield.

Step c: Preparation of (2R,2S) (1α,5α,6α)-N-[3-tert-butyloxycarbonyl-3-azabicyclo[3.1.0]hex-6-yl methyl)-2-cyclopentyl-2-hydroxy-N-methyl-2-phenyl acetamide To a solution of trimethylsilyl derivative (2.0 g, 4.1 mmol) and n-tetrabutyl ammonium iodide (0.11 gm, 0.3 mmol) in dry tetrahydrofuran (THF) (20.9 ml) at 0° C., sodium hydride (0.6 g, 12.3 mmol) was added in portion and the resulting solution was stirred at 0° C. for 15 minutes and allowed to cool to room temperature and stirred for 1 hours at RT. Again cooled to 0° C. and methyl iodide (2.3 ml, 36.8 mmol) in dry THF (2.0 ml) was added dropwise. Stirred for 12 hrs at RT. Saturated aqueous $NaHCO_3$ solution (10.0 ml) was added organic layer was separated and dried over anhydrous sodium sulfate. Concentrated and the residue was purified by column chromatograph using 15% ethyl acetate in hexane to give the title compound as semisolid in 61% (1.25 g, 2.49 mmol) yield.

Step d: Preparation of (2R,2S) (1α,5α,6α)-N-[3-azabicyclo[3.1.0]hex-6-ylmethyl)-2-cyclopentyl-2-hydroxy-N-methyl-2-phenyl acetamide To a solution of the compound (0.2 g, 0.4 mmol) from the above step in ethanol (5.0 ml), conc.HCl was added dropwise till the pH of the reaction mixture was 2. The reaction mixture was stirred at RT for 24 hrs. Neutralized with saturated aqueous sodium bicarbonate solution. Concentrated under vacuum and the residue was taken in dichloromethane (10.0 ml) and washed with water and brine solution. The organic layer was dried over anhydrous sodium sulfate and concentrated to give the title compound as solid in 54% (0.07 g, 0.21 mmol) yield.

m.p.: 91.5° C.

$^1$H NMR ($CDCl_3$)spectral data showed: δ 7.29-7.42 m, 5H), 5.39 (m, 1H), 2.81-3.52 (m, 10H), 1.11-1.82 (m, 12H)

IR (DCM): 1621.9 $cm^{-1}$

The mass spectrum showed peak of 329 ($MH^+$).

Biological Activity

Radioligand Binding Assays: The affinity of test compounds for $M_2$ and $M_3$ muscarinic receptor subtypes was determined by [$^3$H]-N-methylscopolamine binding studies, using rat heart and submandibular gland, respectively, as described by Moriya et al., (*Life Sci.*, 1999; 64(25):2351-2358) with minor modifications as follows. The membrane preparation was done with the following modifications: a low spin step of 500 g for 10 minutes at 4° C. was used; the buffer was 20 mM HEPES, 10 mM EDTA, at pH 7.4; the high speed spin was done at 40,000 g and the homogenate was passed through a filter gauge before any spinning. The assay conditions were modified as follows: the assay volume was 250 μL; the incubation time was 3 hours; the PE concentration was 0.1%; the filtermat used was GF/B from Wallac; the scintillant used was Supermix from Wallac; the amount of scintillant was 500 μL/well; and the counter used was a 1450 microbeta PLUS, from Wallac.

Membrane preparation: Submandibular glands and heart were isolated and placed in ice cold homogenising buffer (HEPES 20 mM, 10 mM EDTA, pH 7.4) immediately after sacrifice. The tissues were homogenised in 10 volumes of homogenising buffer and the homogenate was filtered through two layers of wet gauze and filtrate was centrifuged at 500 g for 10 min. The supernatant was subsequently centrifuged at 40,000 g for 20 min. The pellet thus obtained was resuspended in same volume of assay buffer (HEPES 20 mM, EDTA 5 mM, pH 7.4) and were stored at −700C until the time of assay.

Ligand binding assay: The compounds were dissolved and diluted in DMSO. The membrane homogenates (150-250 μg protein) were incubated in 250 μl of assay buffer (HEPES 20 mM, pH 7.4) at 24-25° C. for 3 h. Non-specific binding was determined in the presence of 1 μM atropine. The incubation was terminated by vacuum filtration over GF/B fiber filters (Wallac). The filters were then washed with ice cold 50 mM Tris HCl buffer (pH 7.4). The filter mats were dried and bound radioactivity retained on filters was counted. The $IC_{50}$ and $K_d$ were estimated by using the non-linear curve fitting program using G Pad Prism software. The value of inhibition constant $K_i$ was calculated from competitive binding studies by using Cheng & Prusoff equation (*Biochem Pharmacol*, 1973; 22:3099-3108), $K_i=IC_{50}/(1+L/K_d)$, where L is the concentration of [3H]NMS used in the particular experiment. $pK_i=-[\log K_i]$ Functional Experiments Using Isolated Rat Bladder:

Methodology: Animals were euthanized by overdose of urethane and whole bladder was isolated and removed rapidly and placed in ice cold Tyrode buffer with the following composition (mnMol/L) NaCl 137; KCl 2.7; $CaCl_2$ 1.8; $MgCl_2$ 0.1; $NaHCO_3$ 11.9; $NaH_2PO_4$ 0.4; glucose 5.55 and continuously gassed with 95% $O_2$ and 5% $CO_2$.

The bladder was cut into longitudinal strips (3 mm wide and 5-6 mm long) and mounted in 10 ml organ baths at 30° C., with one end connected to the base of the tissue holder and the other end connected to a polygraph through a force displacement transducer. Each tissue was maintained at a constant basal tension of 2 g and allowed to equilibrate for 1 hour during which the PSS was changed every 15 min. At the end of equilibration period the stabilization of the tissue contractile response was assessed with 1 μmol/L of Carbachol consecutively for 2-3 times. Subsequently a cumulative concentration response curve to carbachol ($10^{-9}$ mol/L to $3\times10^{-5}$ mol/L) was obtained. After several washes, once the baseline was achieved, cumulative concentration response curve was obtained in presence of NCE (NCE added 20 min. prior to the second CRC).

The contractile results were expressed as % of control E max. ED50 values were calculated by fitting a non-linear regression curve (Graph Pad Prism). pKB values were calculated by the formula pKB =-log [(molar concentration of antagonist/(dose ratio-1))] where, dose ratio=$ED_{50}$ in the presence of antagonist/$ED_{50}$ in the absence of antagonist.

In vivo experiments using anesthetized rabbit: The effect of test substances was studied on carbachol evoked changes on bladder pressure, heart rate and salivation. Male rabbits weighing 1.2-3 kg were anaesthetized with urethane (1.5 g/kg), and administered as a slow intravenous infusion through the marginal ear vein. The tracheae were cannulated to maintain airway patency. Blood pressure was recorded from the femoral artery by means of a Statham P10 EZ pressure transducer connected to a Grass model 7D polygraph. The heart rate was monitored by a tachograph triggered by the pulse wave of blood pressure. The other femoral artery was cannulated for the administration of carbachol. Test compound and saline were infused intravenously via the femoral vein.

The bladder was exposed through a midline laparotomy and both the ureters were identified, carefully separated and ligated. The ureters were incised proximally to allow free flow of urine from the kidney to the exterior. Bladder neck was gently held and the urethra was traced and separated from the adjoining tissues. PE canula was introduced into the bladder and ligated. The bladder was drained and subsequently filled with 15 ml of warm saline (37° C.). The other end of the intravesical catheter was connected to the Grass model 7D polygraph through a Statham P10 EZ pressure transducer to monitor the bladder pressure. Care was taken to keep the exposed area moist and warm. A period of 30-60 min was allowed for stabilization of parameters subsequent to surgery. Salivation response was assessed by placing preweighed absorbent cotton gauze in the buccal cavity for 2 minutes after carbachol administration.

The effect of the compound on carbachol (1.5 μg/kg, intrarterial) induced changes on blood pressure, heart rate and bladder pressure were observed. At least two stable responses were obtained. These responses were considered as 100%. Subsequently, effect of increasing dose of test compound or vehicle (i.v,12 to 15 min before carbachol challenge) was studied.

The change in bladder pressure, salivation and agonist induced bradycardia were expressed as % change from pretreatment control. $ID_{50}$ values (dose required to inhibit 50% of response) were calculated from non-linear curve fitting for sigmoidal dose response curve using Graph Pad Prism software and values were expressed as μg/kg. The results of the in-vitro and in-vivo tests are listed in Table II and Table III.

TABLE II

| Compd. No. | Receptor Binding Assay | | Functional Assay $pK_B$ |
|---|---|---|---|
| | $M_3$ Pki | $M_2$ pKi | |
| 1 | 9.28 | 7.92 | 9.36 ± 0.17 |
| 2 | 9.5 ± 0.03 | 8.36 ± 0.03 | 9.16 ± 0.18 |
| 4 | 9.65 ± 0.03 | 8.43 ± 0.07 | 9.28 ± 0.2 |
| 5 | 7.5 ± 0.04 | 6.8 ± 0.04 | — |
| 6 | 7.88 ± 0.03 | 7.11 ± 0.07 | 7.8 ± 0.09 |
| 7 | 8.61 | 7.6 | 8.56 ± 0.11 |
| 8 | 8.83 | 7.35 | — |
| 9 | 8.9 | 8.02 | — |
| 10 | 9.5 | 8.2 | 8.73 ± 0.17 |
| 11 | 8.9 | 7.4 | — |
| 12 | 9.04 | 7.6 | — |
| 13 | 8.7 | 7.3 | — |
| 14 | 8.87 | 7.14 | 8.73 ± 0.18 |
| 15 | 10.18 | 9.66 | — |
| 16 | 9.41 | 7.95 | — |
| 17 | 8.87 | 7.3 | — |
| 18 | 9.42 | 8.56 | — |
| Tolterodine | 8.47 | 8.68 | 8.86 ± 0.12 |

TABLE III

| Compound No. | $ID_{50}$ (μg/kg, i.v) | | | Fold Selectivity | |
|---|---|---|---|---|---|
| | Bladder Pressure | Salivary Response | Heart Rate Response | Bladder versus Salivary | Bladder versus Heart Rate |
| Tolterodine | 25.84 ± 4.24 | 32.5 ± 10.02 | 32.54 ± 5.77 | 1.24 ± 0.21 | 1.26 ± 0.19 |
| 2 | 3.93 ± 1.1 | 7.67 ± 1.19 | 21.13 ± 4.47 | 3.08 ± 0.94 | 12.6 ± 5.7 |
| 4 | 2.14 ± 0.42 | 4.66 ± 0.56 | 5.65 ± 0.86 | 2.37 ± 0.22 | 3.43 ± 1.02 |

We claim:
1. A compounds having the structure of Formula I:

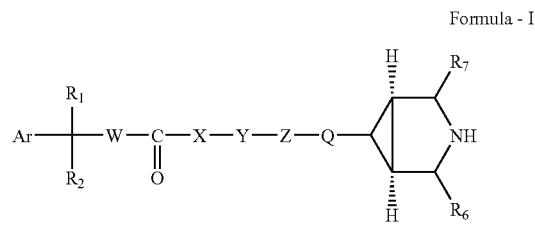

Formula - I and its pharmaceutically acceptable salt, pharmaceutically acceptable enantiomer, diastereomer, or N-oxides wherein Ar represents an aryl ring which may be unsubstituted or substituted by one to three substituents independently selected from lower alkyl ($C_1$-$C_4$), lower perhalo alkyl ($C_1$-$C_4$), cyano, hydroxy, nitro, lower alkoxy ($C_1$-$C_4$), lower perhalo alkoxy ($C_1$-$C_4$), unsubstituted amino, N-lower alkyl ($C_1$-$C_4$) or -aryl amino, amino carbonyl, or N-lower alkyl ($C_1$-$C_4$) or -aryl amino carbonyl;

$R_1$ represents a hydrogen, hydroxy, hydroxy methyl, substituted or unsubstituted amino, alkoxy, carbamoyl or halogen;

$R_2$ represents alkyl, $C_3$-$C_7$ cycloalkyl ring, a $C_3$-$C_7$ cyclo alkenyl ring, an aryl, heterocyclic or a heteroaryl ring having 1 to 2 hetero atoms; the aryl, heteroaryl, heterocyclic or a cycloalkyl ring may be unsubstituted or substituted by one to three substituents independently selected from lower alkyl ($C_1$-$C_4$), lower perhalo alkyl ($C_1$-$C_4$), cyano, hydroxy, nitro, lower alkoxycarbonyl, halogen, lower alkoxy ($C_1$-$C_4$), lower perhalo alkoxy ($C_1$-$C_4$), unsubstituted amino, N-lower alkyl ($C_1$-$C_4$) or -aryl amino, amino carbonyl, or N-lower alkyl ($C_1$-$C_4$) or -aryl amino carbonyl;

W represents $(CH_2)_p$, wherein p represents 0 to 1;

X represents no atom;

Y represents $(CH_2)q$ wherein q represents 0;

Z represents oxygen, sulphur, or $NR_{10}$, wherein $R_{10}$ represents hydrogen or $C_{1-6}$ alkyl;

Q represents —$(CH_2)_n$—, wherein n represents 0 to 4, $CHR_8$, wherein $R_8$ represents H, OH, $C_{1-6}$ alkyl, $C_{1-6}$ alkenyl, or $C_{1-6}$ alkoxy, or Q represents $CH_2CHR_9$, wherein $R_9$ represents H, OH, lower alkyl ($C_1$-$C_4$) or lower alkoxy ($C_1$-$C_4$); and $R_6$ and $R_7$ are independently selected from H, $CH_3$, COOH, $CONH_2$, $NH_2$, and $CH_2NH_2$.

2. The compounds according to claim 1 having the structure of Formula II and their pharmaceutically acceptable salt, pharmaceutically acceptable enantiomers, diastereomers, or N-oxide.

Formula II

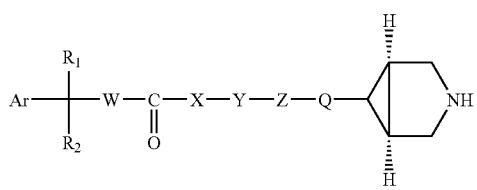

3. The compound according to claim 1 having the structure of Formula III and its pharmaceutically acceptable salt, pharmaceutically acceptable enantiomer, diastereomer, or N-oxide.

Formula III

4. The compound according to claim 1 having the structure of Formula IV and its pharmaceutically acceptable salt, pharmaceutically acceptable enantiomer, diastereomer, or N-oxide, wherein r is 1 to 4.

Formula IV

5. The compound according to claim 1 having the structure of Formula V, and its pharmaceutically acceptable salt, pharmaceutically acceptable enantiomer, diastereomer or N-oxide, wherein s represents 1 to 2.

Formula V

6. A compound selected form the group consisting of (2R,2S) (1α,5α,6α)-N-[3-azabicyclo[3.1.0]hexyl-6-(aminomethyl)-yl]-2-hydroxy-2-cyclopentyl-2-phenyl acetamide (Compound 1);

(2R,2S) (1α,5α,6α)-N-[3-azabicyclo[3.1.0]hexyl-6-(aminomethyl)-yl]-2-hydroxy-2-cyclopentyl-2-phenyl acetamide hydrochloride salt (Compound 2);

(2R)-(1α,5α,6α)-N-[3-azabicyclo[3.1.0]hexyl-6-(aminomethyl)-yl]-2-hydroxy-2-cyclopentyl 2-phenyl acetamide (Compound 3);

(2R)-(1α,5α,6α)-N-[3-azabicyclo[3.1.0]hexyl-6-(aminomethyl)-yl]-2-hydroxy-2-cyclopentyl 2-phenyl acetamide hydrochloride salt (Compound 4);

(2S)-(1α,5α,6α)-N-[3-azabicyclo[3.1.0]hexyl-6-(aminomethyl)-yl]-2-hydroxy-2-cyclopentyl 2-phenyl acetamide (Compound 5);

(2S)-(1α,5α,6α)-N-[3-azabicyclo[3.1.0]hexyl-6-(aminomethyl)-yl]-2-hydroxy-2-cyclopentyl 2-phenyl acetamide hydrochloride salt (Compound 6);

(2R,2S) (1α,5α,6α)-N-[3-azabicyclo[3.1.0]hexyl-6-(aminomethyl)-yl]-2-methoxy-2-cyclopentyl-2-phenyl acetamide (Compound 7);

(2R,2S) (1α,5α,6α)-N-[3-azabicyclo[3.1.0]hexyl-6-(aminomethyl)-yl]-2-hydroxy-2-cycloheptyl-2-phenyl acetamide (Compound 8);

(2R,2S) (1α,5α,6α)-N-[3-azabicyclo[3.1.0]hexyl-6-(aminomethyl)-yl]-2-hydroxy-2-cyclobutyl-2-phenyl acetamide (Compound 9);

(2R,2S) (1α,5α,6α)-N-[3-azabicyclo[3.1.0]hexyl-6-(aminomethyl)-yl]-2-hydroxy-2-cyclobutyl-2-phenyl acetamide tartarate salt (Compound 10);

(2R) (1α,5α,6α)-N-[3-azabicyclo[3.1.0]hexyl-6-(aminomethyl)-yl]-2-hydroxy-2-(3,3-difluorocyclopentyl)-2-phenyl acetamide (Compound 11);

(2R,2S) (1α,5α,6α)-N-[3-azabicyclo[3.1.0]hexyl-6-(aminomethyl)-yl]-2-hydroxy-2-(3-fluorocyclopentyl)-2-phenyl acetamide (Compound 12);

(2R,2S) (1α,5α,6α)-N-[3-azabicyclo[3.1.0]hexyl-6-(aminomethyl)-yl]-2-hydroxy-2-(3,3-difluorocyclopentyl)-2-phenyl acetamide (Compound 13);

(2R,2S) (1α,5α,6α)-N-[3-azabicyclo[3.1.0]hexyl-6-(aminomethyl)-yl]-2-hydroxy-2-(3,3-difluorocyclopentyl)-2-phenyl acetamide tartarate salt (Compound 14);

(2R,2S) (1α,5α,6α)-N-[3-azabicyclo[3.1.0]hexyl-6-(aminomethyl)-yl]-2-hydroxy-2,2-diphenyl acetate (Compound 15);

(2R,2S) (1α,5α,6α)-N-[3-azabicyclo[3.1.0]hexyl-6-(aminomethyl)-yl]-2-hydroxy-2,2-diphenyl acetamide (Compound 16);

(2R,2S) (1α,5α,6α)-N-[3-azabicyclo[3.1.0]hexyl-6-(aminomethyl)-yl]-2-hydroxy-2-cyclohexyl-2-phenyl acetamide (Compound 17) and (2R,2S) (1α,5α,6α)-N-[3-azabicyclo[3.1.0]hex-6-ylmethyl)-2-cyclopentyl-2-hydroxy-N-methyl-2-phenyl acetamide (Compound 18).

7. A pharmaceutical composition comprising a therapeutically effective amount of a compound as defined in claim 1, 2, 3, 4, 5 or 6 together with a pharmaceutically acceptable carrier, excipient or diluent.

* * * * *